US012797389B2

(12) United States Patent
Bordbar

(10) Patent No.: US 12,797,389 B2
(45) Date of Patent: Nov. 17, 2026

(54) TREATING COGNITIVE DISORDERS USING TRAPIDIL

(71) Applicant: Sinopia Biosciences, Inc., San Diego, CA (US)

(72) Inventor: Aarash Bordbar, San Diego, CA (US)

(73) Assignee: SINOPIA BIOSCIENCES, INC., San Diego, CA (US)

(*) Notice: Subject to any disclaimer, the term of this patent is extended or adjusted under 35 U.S.C. 154(b) by 990 days.

(21) Appl. No.: 17/830,073

(22) Filed: Jun. 1, 2022

(65) Prior Publication Data

US 2022/0378794 A1 Dec. 1, 2022

Related U.S. Application Data

(63) Continuation of application No. PCT/US2020/062751, filed on Dec. 1, 2020.

(60) Provisional application No. 62/942,645, filed on Dec. 2, 2019.

(51) Int. Cl.

| | |
|---|---|
| ***A61K 31/519*** | (2006.01) |
| ***A61K 9/00*** | (2006.01) |
| ***A61K 31/53*** | (2006.01) |
| ***A61K 31/5377*** | (2006.01) |
| ***A61K 45/06*** | (2006.01) |
| ***A61P 25/16*** | (2006.01) |

(52) U.S. Cl.

CPC .......... *A61K 31/519* (2013.01); *A61K 9/0019* (2013.01); *A61K 31/53* (2013.01); *A61K 31/5377* (2013.01); *A61K 45/06* (2013.01); *A61P 25/16* (2018.01)

(58) Field of Classification Search

CPC .... A61K 31/519; A61K 9/0019; A61K 31/53; A61K 31/5377; A61K 45/06; A61P 25/16; A61P 25/28

See application file for complete search history.

(56) References Cited

U.S. PATENT DOCUMENTS

| | | | | |
|---|---|---|---|---|
| 4,327,725 | A | 5/1982 | Cortese et al. | |
| 4,624,848 | A | 11/1986 | Lee | |
| 4,968,509 | A | 11/1990 | Radebaugh et al. | |
| 5,456,923 | A | 10/1995 | Nakamichi et al. | |
| 5,461,140 | A | 10/1995 | Heller et al. | |
| 5,516,527 | A | 5/1996 | Curatolo | |
| 5,622,721 | A | 4/1997 | Dansereau et al. | |
| 5,686,105 | A | 11/1997 | Kelm et al. | |
| 5,700,410 | A | 12/1997 | Nakamichi et al. | |
| 5,738,874 | A | 4/1998 | Conte et al. | |
| 5,858,401 | A | 1/1999 | Bhalani et al. | |
| 5,977,175 | A | 11/1999 | Lin | |
| 6,015,578 | A | 1/2000 | Walch | |
| 6,369,065 | B1 | 4/2002 | Chatelain et al. | |
| 6,465,014 | B1 | 10/2002 | Moroni et al. | |
| 6,667,048 | B1 | 12/2003 | Lambert et al. | |
| 6,932,983 | B1 | 8/2005 | Straub et al. | |
| 6,960,563 | B2 | 11/2005 | Egbaria et al. | |
| 10,350,212 | B2 * | 7/2019 | Bordbar | A61P 25/14 |
| 11,628,170 | B2 * | 4/2023 | Bordbar | A61P 25/14 514/567 |
| 12,268,691 | B2 | 4/2025 | Bordbar | |
| 2007/0117765 | A1 | 5/2007 | Sauve et al. | |
| 2013/0317019 | A1 | 11/2013 | Bandak et al. | |
| 2018/0243307 | A1 * | 8/2018 | Bordbar | A61K 9/0053 |
| 2019/0314309 | A1 | 10/2019 | Brown | |
| 2019/0328741 | A1 | 10/2019 | Bordbar | |
| 2023/0201205 | A1 * | 6/2023 | Bordbar | A61K 9/0019 514/567 |
| 2025/0387396 | A1 | 12/2025 | Bordbar | |

FOREIGN PATENT DOCUMENTS

| | | | |
|---|---|---|---|
| EP | 0301423 | A1 | 2/1989 |
| EP | 1666468 | A1 | 6/2006 |
| JP | H02212488 | A | 8/1990 |
| WO | WO-9309781 | A1 | 5/1993 |
| WO | WO-2005026126 | A1 | 3/2005 |
| WO | WO-2006003495 | A1 | 1/2006 |
| WO | WO-2007107843 | A1 | 9/2007 |
| WO | WO-2017176652 | A2 | 10/2017 |
| WO | WO-2021113266 | A1 | 6/2021 |

OTHER PUBLICATIONS

McDaniel KD, Kazee AM, Eskin TA, Hamill RW. Tardive Dyskinesia in Alzheimer's Disease: Clinical Features and Neuropathologic Correlates. Journal of Geriatric Psychiatry and Neurology. 1991;4(2):79-85. doi:10.1177/089198879100400205 (Year: 1991).*

Liu, Y., Stern, Y., Chun, M.R., Jacobs, D.M., Yau, P. and Goldman, J.E. (1997), Pathological correlates of extrapyramidal signs in Alzheimer's disease. Ann Neurol., 41: 368-374. https://doi.org/10.1002/ana.410410312 (Year: 1997).*

Mölsä PK, Marttila RJ, Rinne UK. Extrapyramidal signs in Alzheimer's disease. Neurology. (1984) 34:1114. doi: 10.1212/WNL.34.8.1114 (Year: 1984).*

Arafah, et al., (2023). The Future of Precision Medicine in the Cure of Alzheimer's Disease. Biomedicines, 11(2), 335. https://doi.org/10.3390/biomedicines11020335 (Year: 2023).*

Athanasios et al., Frontiers in Neuroscience,13, 2019, pp. 1-5. https://doi.org/10.3389/fnins.2019.00768 (Year: 2019).*

Strassnig M, Rosenfeld A, Harvey PD. Tardive dyskinesia: motor system impairments, cognition and everyday functioning. CNS Spectrums. 2018;23(6):370-377. doi:10.1017/S1092852917000542 (Year: 2018).*

(Continued)

*Primary Examiner* — James H Alstrum-Acevedo
*Assistant Examiner* — Chantal Adlam
(74) *Attorney, Agent, or Firm* — WILSON SONSINI GOODRICH & ROSATI

(57) ABSTRACT

Disclosed herein are methods, pharmaceutical combinations, and dosage combinations for the prevention or treatment of cognitive disorders with the administration of a therapeutic effective amount of trapidil, a derivative, a metabolite, a prodrug, an analog, or a pharmaceutically acceptable salt thereof. In some embodiments, the trapidil, derivative, metabolite, prodrug, analog, or pharmaceutically acceptable salt thereof is administered in combination with an additional therapeutic agent, such as an antidepressant agent, an antipsychotic agent, an anxiolytic agent, a dopamine precursor, or a dopamine agonist.

20 Claims, 9 Drawing Sheets

(56) References Cited

OTHER PUBLICATIONS

Wu JQ, Chen DC, Xiu MH, Tan YL, Yang FD, Kosten TR, Zhang XY. Tardive dyskinesia is associated with greater cognitive impairment in schizophrenia. Prog Neuropsychopharmacol Biol Psychiatry. Oct. 1, 2013;46:71-7. doi: 10.1016/j.pnpbp.2013.06.013. Epub Jul. 1, 2013. PMID: 23827756. (Year: 2013).*
CAS Registry No. 100557-05-9, 2-[[5-(Diethylamino)[1,2,4]triazolo[1,5-a]pyrimidin-7-yl]pentylamino]ethanol. Retrieved Date: Mar. 21, 2024.
Corsini, A, et al., Trapidil derivatives and low density lipoprotein metabolism by human skin fibroblasts and by human hepatoma cell line Hep G2. Pharmacological Research 21(5):521-31 (1989).
Nakagawa, H, et al., Simultaneous determination of trapidil and its metabolites in serum by high-performance liquid chromatography. Yakugaku Zasshi 104(6):635-9 (1984) (English Abstract).
Osinski, Michael, et al., Pharmacological approaches one Protein kinase A activation to inhibition the mitogenesis of vascular smooth muscle cells. Dissertation Düsseldorf 111 pages (2000).
Walsmann, P, et al., Biochemical and pharmacological aspects of the thrombin inhibitor hirudin. Die Pharmazie 36(10):653,653-660 (1981).
Eiji, Katsunuma, and Arata Koichi. Clinical experience with Rocornal Granules (Trapidil) for chronic cerebrovascular disease. Basics and Clinical Practice 21(12):189-194 (1987) (Summary in English).
Ikui, Kazuyuki. Clinical experience with Trapidil (Rocornal®) for vascular dementia. Medicine and Pharmacy 16(2):609-616 (1986) (Summary in English).
Yoshida, Kunio, and Katsuya Sato. For vascular dementia: Experience with trapidil (Rocornal). Foundations and clinical 19(7):345-352 (1985) (Summary in English).
Frishberg et al. Cell composition analysis of bulk genomics using single-cell data. Nature Methods 16:327-332 (2019).
Gerfen et al. D1 and D2 dopamine receptor-regulated gene expression of striatonigral and striatopallidal neurons. Science 250(4986):1429-1432 (1990).
Gokce et al. Cellular Taxonomy of the Mouse Striatum as Revealed by Single-Cell RNA-Seq. Cell Reports 16:1126-1137 (2016).
Heinroth et al. Influence of Trapidil derivatives on arachidonic acid- and prostaglandin endoperoxide analogue-induced platelet aggregation and thromboxane A2 formation. Biomedica biochimica acta 43(8-9):S389-392 (Abstract only) (1983).
Heinroth-Hoffmann et al. Influence of Trapidil and Trapidil Derivatives on the Content of Cyclic Nucleotides in Human Intima Cells Cultured from Atherosclerotic Plaques. Drug Development Res 19(3):321-327 (1990).
Krause et al. Advances in Pharmacological Research and Practice: Proceedings of the 4th Congress of the Hungarian Pharmacological Society, Budapest, pp. 139-142 (1985).
Liberman et al. Pharmaceutical Dosage Forms. 2nd Ed. vol. 1:209-214 (1990).
Nogrady. Chapter 4: Pro Drugs and Soft Drugs. In: Medicinal Chemistry: A Biochemical approach. New York: Oxford University Press, p. 388-392 (1985).
PCT/US2020/062751 International Search Report and Written Opinion dated Jun. 10, 2021.
PCT/US2020/062751 International Invitation to Pay Additional Fees dated Jun. 10, 2021.
Pfeifer et al. Biotransformation of the Trapidil (rocornal) derivative AR 12463 in the rat. Die Pharmazie 45(8), 609-614 (1990) (English Abstract).
Saulnier et al. An Efficient Method For The Synthesis of Guanidino Prodrugs. Bioorganic and Medicinal Chemistry Letters 4(16):1985-1990 (1994).
Sharma et al. Phosphodiesterases: Regulators of cyclic nucleotide signals and novel molecular target for movement disorders. Eur J Pharmacol . 714(1-3):486-97 (2013).
Silverman et al. Chapter 8: Prodrugs and drug delivery systems. In: The Organic Chemistry of Drug Design and Drug Action. San Diego: Academic Press, Inc. p. 352-401 (1992).
Singh et al. Encyclopedia of Pharmaceutical Technology 2nd Ed. pp. 751-753 (2002).
Singh et al. Encyclopedia of Pharmaceutical Technology 2nd Ed., pp. 754-757 (2002).
Thürmann et al. Pharmacokinetics of the PDGF-antagonist Trapidil in patients with and without renal impairment. Clin Nephrol 47(2):99-105 (Abstract only) (1997).
Database accession No. 100557-04-8. Database Registry [Online] Chemical Abstract Service; Mar. 1, 1986 (Mar. 1, 1986), Anon.: "AR 12463".
Co-pending U.S. Appl. No. 19/025,296, inventor Bordbar; Aarash, filed on Jan. 16, 2025.
Kofler, Michael et al. Working memory deficits and social problems in children with ADHD. Florida State University Libraries. Department of Psychology Faculty Publications J Abnorm Child Psychol 39(6):805-17 (pp. 1-27) (2011).
Smith, R.C. et al. Effects of dopamine agonists in tardive dyskinesia. Am J. Psychiatry 134(7):763-8 (1977).
Xenazine® (tetrabenazine) tablets. Product Label Information. Reference ID: 3774019 (pp. 1-22) (Approval 2008/Revised 2015).

* cited by examiner

TREATING COGNITIVE DISORDERS USING TRAPIDIL

CROSS-REFERENCE

This application is a continuation of International Application No. PCT/US2020/062751, filed Dec. 1, 2020, which claims the benefit of U.S. Patent Application No. 62/942,645, filed Dec. 2, 2019, each of which is hereby incorporated by reference in its entirety.

SUMMARY

Disclosed herein, in certain embodiments, are methods, pharmaceutical combinations, dosage forms, and kits for the treatment of a cognitive disorder or a psychological condition. In some embodiments, the psychological condition comprises clinical depression, anxiety, apathy, lack of motivation, or psychosis. In some embodiments, the treatment comprises use of a therapeutic effective amount of trapidil, a derivative, a metabolite, a prodrug, an analog, or a pharmaceutically acceptable salt thereof of trapidil. In some embodiments, the dosage combinations are provided comprising trapidil and a dopamine agonist or dopamine precursor (e.g., levodopa) for treatment of the cognitive disorders or psychological conditions described herein.

Provided herein, in some embodiments, are methods of treating or preventing a cognitive disorder or psychological condition in a subject in need thereof, comprising administering to the subject a therapeutically effective dose of trapidil, a derivative, a metabolite, a prodrug, an analog, or a pharmaceutically acceptable salt thereof. In some embodiments, the subject has been diagnosed with Parkinson's disease. In some embodiments, the cognitive disorder or the psychological condition is not caused by Parkinson's disease. In some embodiments, the cognitive disorder or the psychological condition is caused, at least in part, by Parkinson's disease. In some embodiments, the cognitive disorder or the psychological condition is not caused by schizophrenia. In some embodiments, the cognitive disorder or the psychological condition is, at least in part, caused by schizophrenia. In some embodiments, the methods described herein further comprise administering to the subject an additional therapeutic agent. In some embodiments, the additional therapeutic agent is a Parkinson's disease therapy. In some embodiments, the cognitive disorder is caused, at least in part, by the therapeutic agent. In some embodiments, the administration of the trapidil treats or prevents the cognitive disorder, caused, at least in part, by the additional therapeutic agent. In some embodiments, the additional therapeutic comprises (a) an antidepressant agent; (b) an antipsychotic agent; (c) anxiolytic agent; (d) a dopamine precursor; (e) a dopamine agonist; or (f) any combination of (a) to (e). In some embodiments, the additional therapeutic agent is a dopamine-precursor. In some embodiments, the dopamine precursor is levodopa. In some embodiments, the additional therapeutic agent is a dopamine agonist. In some embodiments, the dopamine agonist is rotigotine, cabergoline, pergolide, bromocriptine, piribedil, pramipexole, ropinirole, lisuride, quinagolide, and/or apomorphine. In some embodiments, the cognitive disorder is a neurodegenerative disorder. In some embodiments, the cognitive disorder is associated with an antagonist of the N-methyl-D-aspartate receptor (NMDA-R). In some embodiments the cognitive disorder is caused by aberrant dopaminergic signaling caused by neurodegeneration. In some embodiments, the psychological condition is anxiety, depression, apathy, lack of motivation, psychosis, or a combination thereof. In some embodiments, the cognitive disorder is a cognitive impairment. In some embodiments, the cognitive impairment is Mild Cognitive Impairment, and/or dementia. In some embodiments, the cognitive impairment is due to schizophrenia or Attention-deficit/hyperactivity disorder. In some embodiments, the dementia is Alzheimer's disease, senile dementia, Parkinson's disease dementia, Lewy Body dementia, semantic dementia, subcortical dementia, aphasia, Logopenic progressive aphasia, Primary progressive aphasia, Progressive nonfluent aphasia, pseudosenility, apraxia, agnosia, behavioral/personality changes, impaired judgment, amnesia, frontotemporal dementia, frontotemporal dementia and parkinsonism linked to chromosome 17, cognitive vulnerability, cognitive slippage, corticobasal degeneration, corticobasal syndrome, Lewy body disease, or drug/substance induced cognitive decline. In some embodiments, the cognitive impairment comprises a deficit in any of the five cognitive domains: attention, working memory, executive function, visuospatial function, and memory. In some embodiments, the cognitive impairment is an executive function deficit, an attention difficulty, slowed thinking, difficulties in word-finding, difficulties in learning or remembering information, or any combination thereof. In some embodiments, the subject has Parkinson's disease. In some embodiments, the trapidil is N,N-diethyl-5-methyl-[1,2,4]triazolo[1,5-a]pyrimidin-7-amine. In some embodiments, the derivative comprises AR 12455, AR 12456, AR 12460, AR 12463, AR 12464, AR 12465, or AR 12565. In some embodiments, the metabolite comprises desethyl-trapidil, 5-piperidin-4'-olyl-7-[N-pentyl-N-(beta-hydroxyethyl)]amino-s-triazolo[1,5-a]pyrimidine, 5-piperidin-4'-olyl-7-[N-pent-4-olyl-N-(beta-hydroxyethyl)]amino-s-triazolo[1,5-a]pyrimidine, hydroxy- or ketopentyl derivatives, piperidinoles or piperidinones, TP1, or TP2. In some embodiments, the pharmaceutically acceptable salt comprises salts with hydrochloric acid, hydrobromic acid, hydroiodic acid, sulfuric acid, nitric acid, ocalic acid, malonic acid, or tartaric acid. In some embodiments, trapidil, a derivative, a metabolite, a prodrug, an analog, or a pharmaceutically acceptable salt thereof is administered orally. In some embodiments, trapidil, a derivative, a metabolite, a prodrug, an analog, or a pharmaceutically acceptable salt thereof is administered intravenously or subcutaneously. In some embodiments, trapidil, a derivative, a metabolite, a prodrug, an analog, or a pharmaceutically acceptable salt thereof and the additional therapeutic agent are administered simultaneously or sequentially. In some embodiments, trapidil, a derivative, a metabolite, a prodrug, an analog, or a pharmaceutically acceptable salt thereof is administered prior to administration of the additional therapeutic agent or after the administration of the additional therapeutic agent. In some embodiments, the additional therapeutic agent is administered intravenously or subcutaneously. In some embodiments, the additional therapeutic comprises (a) an antidepressant agent; (b) an antipsychotic agent; (c) anxiolytic agent; (d) a dopamine precursor; (e) a dopamine agonist; or (f) any combination of (a) to (e). In some embodiments, the additional therapeutic agent is a dopamine-precursor. In some embodiments, the dopamine precursor is levodopa. In some embodiments, the additional therapeutic agent is a dopamine agonist. In some embodiments, the dopamine agonist is rotigotine, cabergoline, pergolide, bromocriptine, piribedil, pramipexole, ropinirole, lisuride, quinagolide, and/or apomorphine. In some embodiments, the Trapidil, a derivative, a metabolite, a prodrug, an analog, or a pharmaceutically acceptable salt thereof is administered to the subject three times a day.

Provided herein, in some embodiments, are pharmaceutical combinations for use in a therapy for the treatment of a cognitive disorder or associated psychological condition in a subject in need thereof comprising a therapeutic combination of: trapidil, a derivative, a metabolite, a prodrug, an analog, or a pharmaceutically acceptable salt thereof; and an additional therapeutic agent. In some embodiments, the subject has been diagnosed with Parkinson's disease. In some embodiments, the cognitive disorder or the psychological condition is not caused by Parkinson's disease. In some embodiments, the cognitive disorder or the psychological condition is caused, at least in part, by Parkinson's disease. In some embodiments, the cognitive disorder or the psychological condition is not caused by schizophrenia. In some embodiments, the cognitive disorder or the psychological condition is, at least in part, caused by schizophrenia. In some embodiments, the cognitive disorder is caused, at least in part, by the additional therapeutic agent. In some embodiments, the administration of the trapidil treats or prevents the cognitive disorder, caused, at least in part, by the additional therapeutic agent. In some embodiments, the additional therapeutic comprises (a) an antidepressant agent; (b) an antipsychotic agent; (c) anxiolytic agent; (d) a dopamine precursor; (e) a dopamine agonist; or (f) any combination of (a) to (e). In some embodiments, the additional therapeutic agent is a dopamine-precursor. In some embodiments, the dopamine precursor is levodopa. In some embodiments, the additional therapeutic agent is a dopamine agonist. In some embodiments, the additional therapeutic agent is a dopamine agonist. In some embodiments, the dopamine agonist is rotigotine, cabergoline, pergolide, bromocriptine, piribedil, pramipexole, ropinirole, lisuride, quinagolide, and/or apomorphine. In some embodiments, the cognitive disorder is a neurodegenerative disorder. In some embodiments, the cognitive disorder is associated with an antagonist of the N-methyl-D-aspartate receptor (NMDA-R). In some embodiments the cognitive disorder is due to aberrant dopaminergic signaling caused by neurodegeneration. In some embodiments, the psychological condition comprises anxiety, depression, apathy, lack of motivation, or psychosis, or any combination thereof. In some embodiments, the cognitive disorder comprises a cognitive impairment. In some embodiments, the cognitive impairment comprises Mild Cognitive Impairment, and/or dementia. In some embodiments, the cognitive impairment is due to schizophrenia or Attention-deficit/hyperactivity disorder. In some embodiments, the dementia comprises senile dimension, Parkinson's disease dementia, Lewy Body dementia, semantic dementia, subcortical dementia, aphasia, logopenic progressive aphasia, primary progressive aphasia, progressive nonfluent aphasia, pseudosenility, apraxia, agnosia, behavioral/personality changes, impaired judgment, amnesia, frontotemporal dementia, frontotemporal dementia and parkinsonism linked to chromosome 17, cognitive vulnerability, cognitive slippage, corticobasal degeneration, corticobasal syndrome, Lewy body disease, or drug/substance induced cognitive decline. In some embodiments, the cognitive impairment comprises a deficit in any of the five cognitive domains: attention, working memory, executive function, visuospatial function, and memory. In some embodiments, the cognitive impairment is an executive function deficit, an attention difficulty, slowed thinking, difficulties in word-finding, difficulties in learning or remembering information, or any combination thereof. In some embodiments, the trapidil is N,N-diethyl-5-methyl-[1,2,4]triazolo[1,5-a]pyrimidin-7-amine. In some embodiments, the derivative comprises AR 12455, AR 12456, AR 12460, AR 12463, AR 12464, AR 12465, or AR 12565. In some embodiments, the metabolite comprises desethyl-trapidil, 5-piperidin-4'-olyl-7-[N-pentyl-N-(beta-hydroxyethyl)]amino-s-triazolo[1,5-a]pyrimidine, 5-piperidin-4'-olyl-7-[N-pent-4-olyl-N-(beta-hydroxyethyl)]amino-s-triazolo[1,5-a]pyrimidine, hydroxy- or ketopentyl derivatives, piperidinoles or piperidinones, TP1, or TP2. In some embodiments, the pharmaceutically acceptable salt of trapidil comprises salts with hydrochloric acid, hydrobromic acid, hydroiodic acid, sulfuric acid, nitric acid, ocalic acid, malonic acid, or tartaric acid. In some embodiments, trapidil, a derivative, a metabolite, a prodrug, an analog, or a pharmaceutically acceptable salt thereof is administered orally. In some embodiments, trapidil, a derivative, a metabolite, a prodrug, an analog, or a pharmaceutically acceptable salt thereof is administered intravenously or subcutaneously. In some embodiments, trapidil, a derivative, a metabolite, a prodrug, an analog, or a pharmaceutically acceptable salt thereof and the additional therapeutic agent are administered simultaneously or sequentially. In some embodiments, trapidil, a derivative, a metabolite, a prodrug, an analog, or a pharmaceutically acceptable salt thereof is administered prior to administration of the additional therapeutic agent or after the administration of the additional therapeutic agent. In some embodiments, the pharmaceutical combination further comprises at least one pharmaceutically acceptable: excipient, carrier, or diluent. In some embodiments, the pharmaceutical combination is in a fixed-dosage combination and further comprising at least one pharmaceutically acceptable: excipient, carrier, or diluent. In some embodiments, the Trapidil, a derivative, a metabolite, a prodrug, an analog, or a pharmaceutically acceptable salt thereof is administered to the subject three times a day.

Provided herein, in some embodiments, are dosage combinations for use in a treatment of a cognitive disorder or psychological condition in a subject in need thereof, comprising administering to the subject a therapeutically effective combination of: trapidil, a derivative, a metabolite, a prodrug, an analog, or a pharmaceutically acceptable salt thereof; and an additional therapeutic agent. In some embodiments, the subject has been diagnosed with Parkinson's disease. In some embodiments, the cognitive disorder or the psychological condition is not caused by Parkinson's disease. In some embodiments, the cognitive disorder or the psychological condition is caused, at least in part, by Parkinson's disease. In some embodiments, the cognitive disorder or the psychological condition is not caused by schizophrenia. In some embodiments, the cognitive disorder or the psychological condition is, at least in part, caused by schizophrenia. In some embodiments, the additional therapeutic agent is a Parkinson's disease therapy. In some embodiments, the cognitive disorder is caused, at least in part, by the additional therapeutic agent. In some embodiments, the administration of the trapidil treats or prevents the cognitive disorder, caused, at least in part, by the additional therapeutic agent. In some embodiments, the additional therapeutic comprises (a) an antidepressant agent; (b) an antipsychotic agent; (c) anxiolytic agent; (d) a dopamine precursor; (e) a dopamine agonist; or (f) any combination of (a) to (e). In some embodiments, the additional therapeutic agent is a dopamine-precursor. In some embodiments, the dopamine precursor is levodopa. In some embodiments, the additional therapeutic agent is a dopamine agonist. In some embodiments, the dopamine agonist is rotigotine, cabergoline, pergolide, bromocriptine, piribedil, pramipexole, ropinirole, lisuride, quinagolide, and/or apomorphine. In some embodiments, the cognitive disorder is a neurodegenerative disorder. In some embodiments, the cognitive disorder is associated with an antagonist of the N-methyl-D-aspartate receptor (NMDA-R). In some embodiments the cognitive disorder is aberrant dopaminergic signaling caused by neurodegeneration. In some embodiments, the psychological condition comprises anxiety, depression, apathy, lack of motivation, or psychosis, or any combination thereof. In some embodiments, the cognitive disorder comprises a cognitive impairment. In some embodiments, the cognitive impairment comprises Mild Cognitive Impairment, and/or dementia. In some embodiments, the cognitive impairment is due to schizophrenia or Attention-deficit/hyperactivity disorder (ADHD). In some embodiments, the dementia comprises Alzheimer's disease, senile dementia, Parkinson's disease dementia, Lewy Body dementia, semantic dementia, subcortical dementia, aphasia, logopenic progressive aphasia, primary progressive aphasia, progressive nonfluent aphasia, pseudosenility, apraxia, agnosia, behavioral/personality changes, impaired judgment, amnesia, frontotemporal dementia, frontotemporal dementia and parkinsonism linked to chromosome 17, cognitive vulnerability, cognitive slippage, corticobasal degeneration, corticobasal syndrome, Lewy body disease, or drug/substance induced cognitive decline. In some embodiments, the cognitive impairment comprises a deficit in any of the five cognitive domains: attention, working memory, executive function, visuospatial function, and memory. In some embodiments, the cognitive impairment is an executive function deficit, an attention difficulty, slowed thinking, difficulties in word-finding, difficulties in learning or remembering information, or any combination thereof. In some embodiments, the trapidil is N,N-diethyl-5-methyl-[1,2,4]triazolo[1,5-a]pyrimidin-7-amine. In some embodiments, the derivative comprises AR 12455, AR 12456, AR 12460, AR 12463, AR 12464, AR 12465, or AR 12565. In some embodiments, the metabolite comprises desethyl-trapidil, 5-piperidin-4'-olyl-7-[N-pentyl-N-(beta-hydroxyethyl)]amino-s-triazolo[1,5-a]pyrimidine, 5-piperidin-4'-olyl-7-[N-pent-4-olyl-N-(beta-hydroxyethyl)]amino-s-triazolo[1,5-a]pyrimidine, hydroxy- or ketopentyl derivatives, piperidinoles or piperidinones, TP1, or TP2. In some embodiments, the pharmaceutically acceptable salt comprises salts with hydrochloric acid, hydrobromic acid, hydroiodic acid, sulfuric acid, nitric acid, ocalic acid, malonic acid, or tartaric acid. In some embodiments, trapidil, a derivative, a metabolite, a prodrug, an analog, or a pharmaceutically acceptable salt thereof is administered orally. In some embodiments, trapidil, a derivative, a metabolite, a prodrug, an analog, or a pharmaceutically acceptable salt thereof is administered intravenously or subcutaneously. In some embodiments, trapidil, a derivative, a metabolite, a prodrug, an analog, or a pharmaceutically acceptable salt thereof and the additional therapeutic agent are administered sin separate or unified dosage forms In some embodiments, trapidil, a derivative, a metabolite, a prodrug, an analog, or a pharmaceutically acceptable salt thereof is administered prior to administration of the additional therapeutic agent or after the administration of the additional therapeutic agent. In some embodiments, the dosage combination further comprises at least one pharmaceutically acceptable: excipient, carrier, or diluent. In some embodiments, the dosage combination is in a fixed-dosage combination and further comprising at least one pharmaceutically acceptable: excipient, carrier, or diluent. In some embodiments, the dosage combination is administered to the subject three times a day.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the inventive aspects are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9A shows that acute administration of PCP (7.5 mg/kg, IP) induced working memory deficits as detected by decreased percentage of spontaneous alternations in mice and shows oral administration of trapidil was able to correct the observed deficits at several different doses. FIG. 9B shows that administration of trapidil does not significantly impact the number of entries, showing that there is no confounding effect. Compared to vehicle: *p<0.1, p<0.05, *p<0.01, Compared to phencyclidine treatment: #p<0.1, ##p<0.05, ###p<0.01

DETAILED DESCRIPTION

Figure 1:
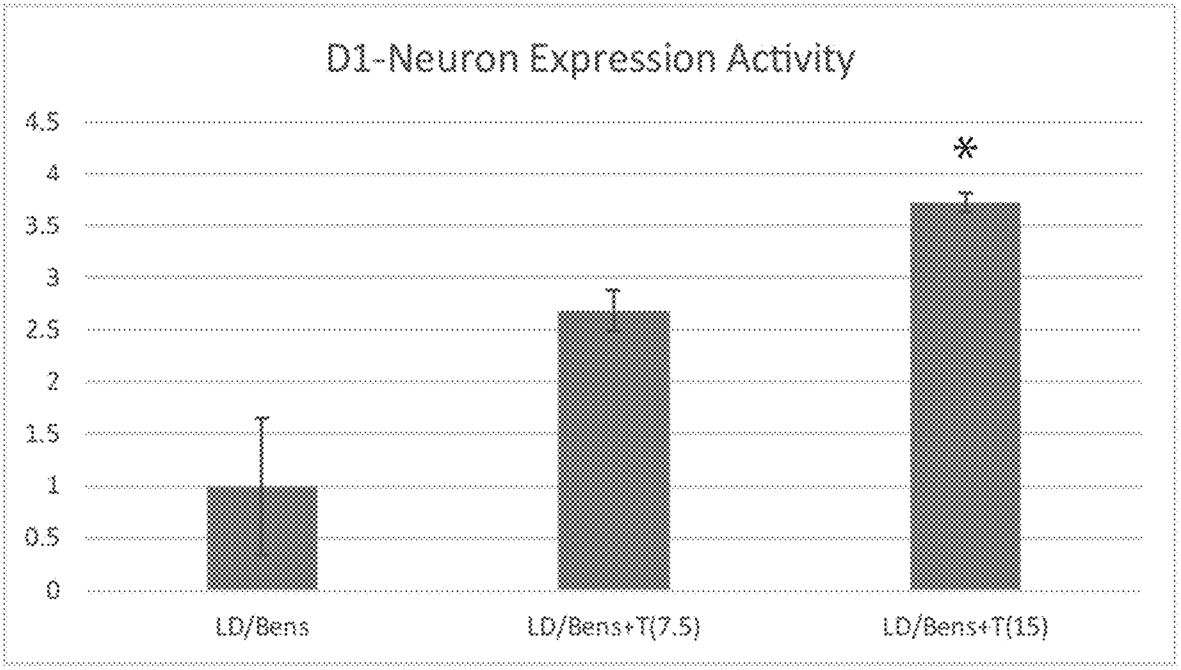
FIG. 1 exemplifies trapidil's ability to increase expression of neurons expressing D1 receptors (*–p<0.05).

Cognitive disorders (e.g., cognitive impairments, cognitive deficits, cognitive conditions) in many cases affect a subject's ability to make decisions, learn new things, concentrate, or remember. Cognitive disorders can range from mild to severe with impacts on everyday activities, leading to the loss of ability to independently function. Cognitive disorders described here are worsened by pre-existing conditions, including neurological disorders such as Parkinson's disease and schizophrenia. For many individuals with cognitive disorders, psychological conditions can also develop, such as anxiety, clinical depression, apathy, and lack of motivation. The combination of cognitive disorders and psychological conditions can have a confounding effect on patient outcomes.

Cognitive disorders and psychological conditions affect millions of people in the United States. It is estimated that 16 million Americans live with cognitive disorders, with most of these patients being 65 years or older. This number of individuals living with cognitive disorders is expected to increase with the growing aging population. This imminent growth in number will place significant burdens on the health care system. Nearly 80% of patients with preexisting conditions, such as Parkinson's disease, develop some form of a cognitive disorder. Nearly one in five adults in the United States live with a psychological condition (51.50 million Americans in 2019).

Cognitive disorders can also be drug-induced. For example, many Parkinson's disease patients, receiving high levels of levodopa, the gold standard of care to treat motor symptoms of Parkinson's disease, can have increased risk for developing a cognitive disorder. The administration of levodopa produces continuous dopaminergic stimulation of striatal dopamine receptors. Initially, cognitive disorders in Parkinson's disease patients respond well to (e.g., are alleviated or prevented by) dopaminergic stimulation by levodopa. However, hyperactivation of dopamine receptors caused by escalating doses of levodopa can worsen cognition in Parkinson's disease patients over time. In addition, excessive dopaminergic stimulation can have adverse effects according to a "U-shape" curve where too little or too much dopamine causes a cognitive disorder in the Parkinson's disease patient. To address loss of response to levodopa in Parkinson's disease patients, doses increase over the lifetime of the patient, which in some cases can be many years. For early onset Parkinson's disease patients, developing a cognitive disorder or a psychological conditions resulting from your treatment regimen may be inevitable.

Thus, there is a need for a therapeutic strategy that is effective to treat cognitive disorders and/or psychological conditions. This need is particularly acute for patients who suffer from conditions in which cognitive deficits are part of the symptoms or from preexisting conditions that increase the likelihood of developing a cognitive disorder or psychological condition (e.g., schizophrenia, Parkinson's disease), and for which the gold standard of care worsens (or in some cases causes) the cognitive disorder of psychological condition to begin with.

Trapidil is a vasodilator and antiplatelet drug that has been used for the treatment of ischemic coronary heart, liver, and kidney disease. trapidil is a reported potentiator of protein kinase A regulatory subunit 2 (PRKAR2A and PRKAR2B). trapidil's reported mechanism of action is not shared with known therapeutic agents used to treat cognitive disorders or psychological conditions, such as cognitive enhancing drugs (acetylcholinesterase inhibitors), anti-psychotics, anti-depressants, and anti-anxiety medications.

Unexpectedly, the inventors of the present disclosure determined through single cell deconvolution computational analysis, that trapidil modulates neurons expressing dopamine 1 receptors in Parkinson's disease animal models, even though trapidil is not a known dopamine 1 receptor agonist. As shown in Example 1, trapidil induces large gene expression changes in neurons expressing dopamine 1 receptors but not expressing dopamine 2 receptors. Such selective changes in gene expression are similar to dopamine 1 agonists. In some embodiments, administering to a subject a therapeutically effective dose of trapidil activates neurons expressing dopamine 1 receptors and/or modulates neurons expressing dopamine 1 receptors. In some embodiments, the activation and/or modulation of neurons expressing dopamine 1 receptors (e.g., induced by the administration of a therapeutically effective amount of trapidil) prevents aberrant dopamine signaling. In some embodiments, the activation and/or modulation of neurons expressing dopamine 1 receptors (e.g., induced by the administration of a therapeutically effective amount of trapidil) treats or prevents a cognitive disorders and/or psychological conditions in a subject, for example, a subject with Parkinson's disease. In some embodiments, the cognitive disorder is caused, at least in part, by Levodopa or another dopamine precursor or dopamine agonist administered to treat Parkinson's disease in the subject.

The inventors of the present disclosure discovered that administration of trapidil alone, or in combination with levodopa, increases cognitive performance in non-human primate studies. In addition, it was observed that animals administered trapidil show improved total response time and accuracy of response. This decrease in response time suggests an improvement in motivation and/or processing speed. Without being bound by any particular theory, it is believed that observed improvement in motivation may correct a psychological condition of apathy. Apathy is among many psychological conditions that is highly correlated with cognitive impairments, such as those common among Parkinson's disease patients, and can serve as a predictor of potential cognitive decline in these patients.

The inventors also show herein that administration of trapidil also improves cognitive deficits observed in murine models of schizophrenia. Mice administered trapidil show improved percentages of spontaneous alternations in the Y-maze behavioral test, suggesting improved working memory.

Disclosed herein, in certain embodiments, are methods of treating or preventing cognitive disorders or psychological conditions with trapidil, a derivative, a metabolite, a prodrug, an analog, or a pharmaceutically acceptable salt thereof. In some embodiments, the subject has Parkinson's disease. In some embodiments, the cognitive disorder or psychological disorder is not caused by, or associated with the Parkinson's disease. In some embodiments, the subject has schizophrenia. Also disclosed herein are pharmaceutical combinations or dosage combinations comprising trapidil, a derivative, a metabolite, a prodrug, an analog, or a pharmaceutically acceptable salt thereof; and an additional therapeutic agent. In some embodiments, the additional therapeutic comprises (a) an antidepressant agent; (b) an antipsychotic agent; (c) anxiolytic agent; (d) a dopamine precursor; (e) a dopamine agonist; or (f) any combination of (a) to (e). The additional therapeutic agent, in some embodiments, is a dopamine precursor (e.g., levodopa). In some embodiments, the additional therapeutic agent is a combination therapy of a dopamine precursor (e.g., levodopa) and adjunctive therapy (e.g., carbidopa). In some embodiments, the additional therapeutic agent is a dopamine agonist (e.g., rotigotine, cabergoline, pergolide, bromocriptine, piribedil, pramipexole, ropinirole, lisuride, quinagolide, or apomorphine). In some embodiments, the pharmaceutical combination is therapeutically effective to treat or prevent the cognitive disorder or the psychological condition in the subject. In some embodiments, the pharmaceutical combination further comprises at least one pharmaceutically acceptable: excipient, carrier, or diluent. In some embodiments, the pharmaceutical combination is in a fixed-dosage combination.

I. METHODS OF TREATMENT

Disclosed herein, in certain embodiments, are methods of treating or preventing cognitive disorders or psychological conditions with a therapeutic agent, or combination of therapeutic agents, described herein. In some embodiments, the therapeutic agent is trapidil, a derivative, a metabolite, a prodrug, an analog, or a pharmaceutically acceptable salt thereof. In some embodiments, the subject has Parkinson's disease or schizophrenia. In some embodiments, the subject has drug-induced cognitive disorder, such as a cognitive impairments. In some embodiments, the drug that induced cognitive impairments is a dopamine precursor (e.g. levodopa) or a dopamine agonist. In some embodiments, the subject has schizophrenia. In some embodiments, the methods further comprise administering an additional therapeutic agent. In some embodiments, the additional therapeutic agent is a dopamine precursor (e.g., levodopa). In some embodiments, the additional therapeutic agent is a combination therapy of a dopamine precursor (e.g., levodopa) and adjunctive therapy (e.g., carbidopa). In some embodiments, the additional therapeutic agent is a dopamine agonist (e.g., rotigotine, cabergoline, pergolide, bromocriptine, piribedil, pramipexole, ropinirole, lisuride, quinagolide, or apomorphine). In some embodiments, the pharmaceutical combination is therapeutically effective to treat or prevent the cognitive disorder or the psychological condition in the subject. In some embodiments, the subject is a human. In some embodiments, the trapidil, the derivative, the metabolite, the prodrug, the analog, or the pharmaceutically acceptable salt thereof, and the additional therapeutic agent (e.g., levodopa) are administered together (e.g., combined dosage form) or separately. In some embodiments, a dose of at most 200 milligrams of trapidil is administered to the subject.

A. Diseases and Conditions

1. Cognitive Disorders

Cognitive disorders comprise a category of mental health disorders that primarily affect cognitive abilities such as learning, memory, perception, or problem solving. In some embodiments, cognitive disorders include cognitive impairments, such as, for example, Mild Cognitive Impairment (e.g., a stage between the expected cognitive decline of normal aging and dementia), and/or dementia. Non-limiting examples of dementia include Alzheimer's disease, Parkinson's dementia, senile dementia, and Lewy Body Dementia. In some embodiments, cognitive impairment, (e.g., Mild Cognitive Impairment) comprises a deficit in any of the following five cognitive domains: attention, working memory, executive function, visuospatial function, and memory. In some embodiments, attention deficits affect a subject's ability to concentrate and focus. In some embodiments, executive function deficits affect a subject's ability to multitask, problem solve. In some embodiments, visuospatial skill deficits affect a subject's ability to see information three dimensionally, such as inability to judge distances or make a mental map for a route. In some embodiments, cognitive impairments (e.g., Mild Cognitive Impairment) are executive function deficits, attention difficulties, slowed thinking, difficulties in word-finding, and/or difficulties in learning or remembering information.

In some embodiments, the cognitive disorder is associated with, or caused by, a therapeutic agent for treatment of a disease or a condition other than a cognitive disorder or psychological condition (e.g., Parkinson's disease). In some embodiments, the therapeutic agent that causes, or is associated with, the cognitive disorder or psychological condition is a dopamine precursor or a dopamine agonist. In some embodiments, the therapeutic agent that causes, or is associated with, the cognitive disorder or psychological condition is pramipexole, ropinirole, rotigotine, pergolide, bromocriptine, piribedile, bromocriptine, lisuride, apomorphine, levodopa, entacapone, tolcapone, selegiline and/or rasagiline. In some embodiments the drug that causes, or is associated with, the cognitive disorder or psychological condition is an N-methyl-D-aspartate receptor antagonist.

In some embodiments, the cognitive disorder comprises Parkinson's disease dementia, semantic dementia, subcortical dementia, postoperative cognitive dysfunction, memory loss, aphasia, Logopenic progressive aphasia, Primary progressive aphasia, Progressive nonfluent aphasia, pseudosenility, apraxia, agnosia, behavioral/personality changes, impaired judgment, amnesia, frontotemporal dementia, frontotemporal dementia and parkinsonism linked to chromosome 17, cognitive vulnerability, cognitive slippage, corticobasal degeneration, corticobasal syndrome, Lewy body disease, or drug/substance induced cognitive decline. In some embodiments, the cognitive impairment is due to schizophrenia or Attention-deficit/hyperactivity disorder. In some embodiments, the cognitive disorder is not caused by Parkinson's disease.

2. Psychological Conditions

Psychological conditions described herein comprise mental conditions affecting the emotional or mental state of a subject (e.g., how a person thinks, feels, behaves). In some embodiments, the psychological condition described herein comprises anxiety, depression, apathy, lack of motivation, or psychosis, or any combination thereof. In some embodiments, the psychological condition comprises a psychological disorder, such as schizophrenia or bipolar disorder. In some embodiments, the psychological condition is clinically diagnosed. In some embodiments, the psychological condition is not caused by Parkinson's disease.

B. Subjects

The subject disclosed herein is a mammal, such as for example a human, mouse, rat, guinea pig, rabbit, non-human primate, or farm animal. In some embodiments, the subject is human. In some embodiments, the subject is a patient who is diagnosed with the disease or condition disclosed herein. In some embodiments, the subject is not diagnosed with the disease or condition. In some embodiments, the disease or condition is a cognitive impairment or psychological condition described herein.

In some embodiments, the subject has Parkinson's disease. In some embodiments, the subject does not have Parkinson's disease. In some embodiments, the subject has been diagnosed with Parkinson's disease. The four primary motor symptoms of Parkinson's disease: tremor, rigidity, bradykinesia (slow movement) and postural instability (balance problems). Observing two or more of these symptoms in the subject is a suitable method of diagnosing Parkinson's disease. Suitable methods also include performing a specific single-photon emission computerized tomography (SPECT) scan (e.g., a dopamine transporter scan (DaTscan)).

In some embodiments, the subject has schizophrenia. In some embodiments, the subject does not have schizophrenia. In some embodiments, the subject has been diagnosed with schizophrenia. If a subject exhibits for a month at least two of: delusions, hallucinations, disorganized speech and behavior, catatonic daze, or bizarre/hyperactive behavior, the subject may be diagnosed with schizophrenia.

C. Therapeutic Agents

1. Trapidil Compounds

Disclosed herein, in some embodiments, are therapeutic agents comprising trapidil that are useful for the treatment of a disease or a condition described herein, such as a cognitive impairment or disorder, or a psychological condition, in a subject disclosed herein. In some embodiments, the subject has Parkinson's disease. In some embodiments, the therapeutic agents comprise an additional therapeutic agent, such as a dopamine precursor (e.g., levodopa). Also provided, in some embodiments, are pharmaceutical compositions comprising trapidil, and optionally, an additional therapeutic agent (e.g., levodopa).

trapidil, a triazolopyrimidine, belongs to a class of anti-anginal and antiplatelet drugs. As demonstrated in Example 1, trapidil is shown to modulate the gene expression of neurons expressing dopamine 1 receptors.

trapidil has the IUPAC name N,N-diethyl-5-methyl-[1,2,4]triazolo[1,5-a]pyrimidin-7-amine and the following chemical structure:

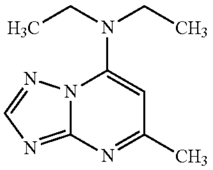

In some embodiments, trapidil also has the names AR 12008, Avantrin, Trapymin, Trapymine, Trapidilum, Angichromen, Estelinol, Karnachol, Perucarate, Rocornal, trapidil Towa Yakuhin, and Travisco. In additional instances, trapidil is referred to herein as SB-0107.

In some embodiments, trapidil derivatives include, but are not limited to, AR 12455, AR 12456, AR 12460, AR 12463, AR 12464, AR 12465, or AR 12565.

In some embodiments, trapidil derivatives include, but are not limited to,

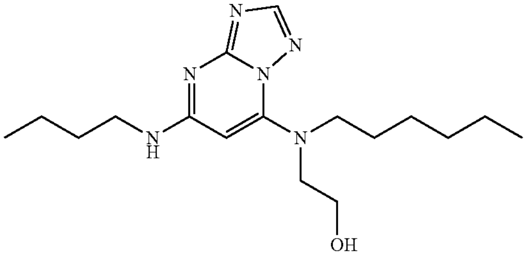

( AR 12456 ),

-continued

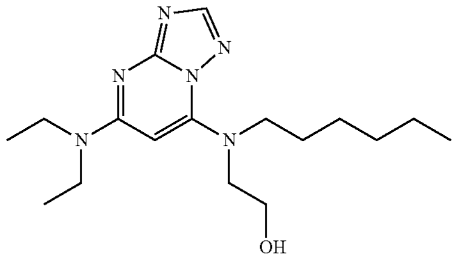

( AR 12460 ),

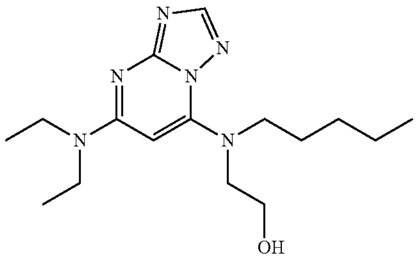

( AR 12463 ),

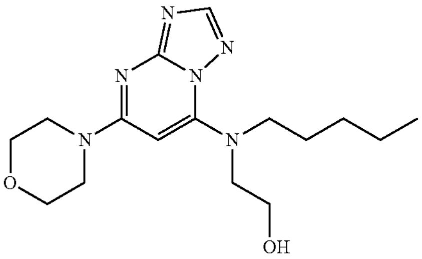

( AR 12464 ),

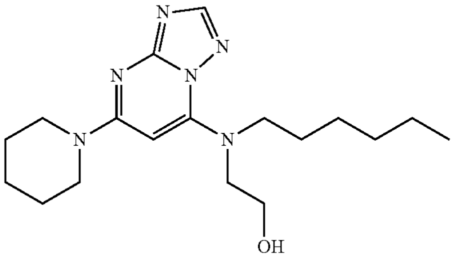

( AR 12465 ),

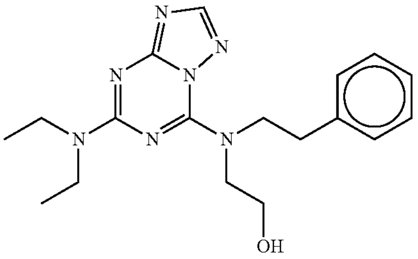

( AR 12565 ), or

-continued

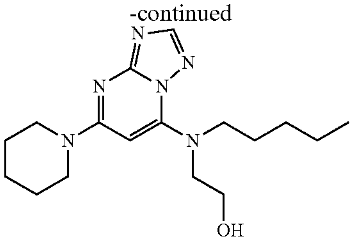

(5-piperidino-7-(N-(n-amyl)-N-(beta-hydroxyethyl)-amino)-s-triazolo(1,5-a)pyrimidine)), In some embodiments, AR 12455 is 5-n-butylamino-7-[N-(n-hexyl)-N-(beta-hydroxyethyl)-amino]-s-triazolo-[1,5-a]pyrimidine. In some embodiments, AR 12456 is 5-di ethyl amino-7-[N-(n-hexyl)-N-(beta-hydroxyethyl)amino]-s-triazolo-[1,5-a]pyrimidine. In some embodiments, AR 12460 is 2-((5-(diethylamino)-[1,2,4]triazolo[1,5-a]pyrimidin-7-yl)(hexyl)amino)ethan-1-ol. In some embodiments, AR 12463 is 5-morpholino-7-[N-amyl-N-(beta-hydroxyethyl)aminol-s-triazolo-[1,5-a]pyrimidine. In some embodiments, AR 12464 is 5-morpholino7-[N-(n-butyl)-N-(beta-hydroxyethyl)amino]-s-triazolo-[1,5-a]pyrimidine. In some embodiments, AR 12465 is 5-piperidino-7-[N-hexyl-N-(beta-hydroxyethyl)amino]-s-triazolo-[1,5-a]pyrimidine. In some embodiments, AR 12565 is 2-((5-(diethylamino)-[1,2,4]triazolo[1,5-a][1,3,5]triazin-7-yl)(phenethyl)amino) ethan-1-ol.

In some embodiments, trapidil metabolites include, but are not limited to, desethyl-trapidil, 5-piperidin-4'-olyl-7-[N-pentyl-N-(beta-hydroxyethyl)]amino-s-triazolo[1,5-a] pyrimidine, 5-piperidin-4'-olyl-7-[N-pent-4-olyl-N-(beta-hydroxyethyl)]amino-s-triazolo[1,5-a]pyrimidine, hydroxy- or ketopentyl derivatives, piperidinoles or piperidinones,

TP-1

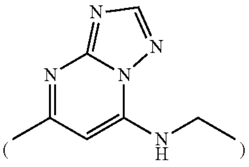

or

TP-2

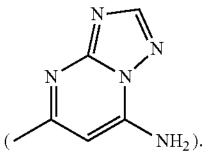

.

In some embodiments, pharmaceutically acceptable salts of trapidil include, but are not limited to, salts with hydrochloric acid, hydrobromic acid, hydroiodic acid, sulfuric acid, nitric acid, ocalic acid, malonic acid, or tartaric acid.

In some embodiments, trapidil is a trapidil disclosed in U.S. Pat. No. 6,015,578; European Patent No. 0301423; or PCT Publication No. WO1993/009781.

In some embodiments, trapidil is a trapidil derivative disclosed in Heinroth-Hoffmann et al. (1990) "Influence of trapidil and trapidil Derivatives on the Content of Cyclic Nucleotides in Human Intima Cells Cultured from Atherosclerotic Plaques," Drug Development Research, 19(3), 321-327; Heinroth et al. (1983) "Influence of trapidil derivatives on arachidonic acid- and prostaglandin endoperoxide analogue-induced platelet aggregation and thromboxane A2 formation," Biomedica biochimica acta, 43(8-9), S389-92; or Krause et al. (1985) Advances in Pharmacological Research and Practice: Proceedings of the 4th Congress of the Hungarian Pharmacological Society, Budapest, pages 139-142.

In some embodiments, trapidil is a trapidil metabolite disclosed in Thürmann et al. (1997) "Pharmacokinetics of the PDGF-antagonist trapidil in patients with and without renal impairment," Clinical nephrology, 47(2), 99-105; or Pfeifer et al. (1990) "Biotransformation of the trapidil (rocornal) derivative AR 12463 in the rat," Die Pharmazie, 45(8), 609-614.

In some embodiments, trapidil is a trapidil salt disclosed in U.S. Pat. No. 6,369,065.

In some embodiments, also disclosed herein is a method of treating a patient by modulating neurons expressing dopamine 1 receptors with administration of a therapeutic effective dose of trapidil, a derivative, a metabolite, a prodrug, an analog, or a pharmaceutically acceptable salt thereof.

In some embodiments, trapidil, a derivative, a metabolite, a prodrug, an analog, or a pharmaceutically acceptable salt thereof is administered as oral, parenteral (e.g., intravenous, subcutaneous, intramuscular), intranasal, buccal, topical, rectal, or transdermal administration. In some embodiments, trapidil, a derivative, a metabolite, a prodrug, an analog, or a pharmaceutically acceptable salt thereof is administered as an oral administration. In some embodiments, trapidil, a derivative, a metabolite, a prodrug, an analog, or a pharmaceutically acceptable salt thereof is administered as a parenteral (e.g., intravenous, subcutaneous, intramuscular) administration. In other cases, trapidil, a derivative, a metabolite, a prodrug, an analog, or a pharmaceutically acceptable salt thereof is administered as a transdermal administration.

In some embodiments, trapidil, a derivative, a metabolite, a prodrug, an analog, or a pharmaceutically acceptable salt thereof is administered orally. In some embodiments, the oral dose ranges from about 10 mg per day to about 3000 mg per day. In some embodiments, the oral dose range is from about 10 mg per day to about 2900 mg per day, from about 10 mg per day to about 2800 mg per day, from about 10 mg per day to about 2700 mg per day, from about 10 mg per day to about 2600 mg per day, from about 10 mg per day to about 2500 mg per day, from about 10 mg per day to about 2400 mg per day, from about 10 mg per day to about 2300 mg per day, from about 10 mg per day to about 2200 mg per day, from about 10 mg per day to about 2100 mg per day, from about 10 mg per day to about 2000 mg per day, from about 10 mg per day to about 1900 mg per day, from about 10 mg per day to about 1800 mg per day, from about 10 mg per day to about 1700 mg per day, from about 10 mg per day to about 1600 mg per day, from about 10 mg per day to about 1500 mg per day, from about 10 mg per day to about 1400 mg per day, from about 10 mg per day to about 1300 mg per day, from about 10 mg per day to about 1200 mg per day, from about 10 mg per day to about 1100 mg per day, from about 10 mg per day to about 1000 mg per day, from about 10 mg per day to about 950 mg per day, from about 10 mg per day to about 900 mg per day, from about 10 mg per day to about 850 mg per day, from about 10 mg per day to about 800 mg per day, from about 10 mg per day to about 750 mg per day, from about 10 mg per day to about 700 mg per day, from about 10 mg per day to about 650 mg per day, from about 10 mg per day to about 600 mg per day, from about 10 mg per day to about 550 mg per day, from about 10 mg per day to about 500 mg per day, from about 10 mg per day to about 450 mg per day, from about 10 mg per day to about 400 mg per day, from about 10 mg per day to about 350 mg per day, from about 10 mg per day to about 300 mg per day, from about 10 mg per day to about 250 mg per day, from about 10 mg per day to about 200 mg per day, from about 10 mg per day to about 150 mg per day, from about 10 mg per day to about 100 mg per day, from about 50 mg per day to about 3000 mg per day, from about 100 mg per day to about 3000 mg per day, from about 150 mg per day to about 3000 mg per day, from about 200 mg per day to about 3000 mg per day, from about 300 mg per day to about 3000 mg per day, from about 400 mg per day to about 3000 mg per day, from about 500 mg per day to about 3000 mg per day, from about 600 mg per day to about 3000 mg per day, from about 700 mg per day to about 3000 mg per day, from about 800 mg per day to about 3000 mg per day, from about 900 mg per day to about 3000 mg per day, from about 1000 mg per day to about 3000 mg per day, from about 1100 mg per day to about 3000 mg per day, from about 1200 mg per day to about 3000 mg per day, from about 1300 mg per day to about 3000 mg per day, from about 1400 mg per day to about 3000 mg per day, from about 1500 mg per day to about 3000 mg per day, from about 1600 mg per day to about 3000 mg per day, from about 1700 mg per day to about 3000 mg per day, from about 1800 mg per day to about 3000 mg per day, from about 1900 mg per day to about 3000 mg per day, from about 2000 mg per day to about 3000 mg per day, from about 2100 mg per day to about 3000 mg per day, from about 2200 mg per day to about 3000 mg per day, from about 2300 mg per day to about 3000 mg per day, from about 2400 mg per day to about 3000 mg per day, from about 2500 mg per day to about 3000 mg per day, from about 2600 mg per day to about 3000 mg per day, from about 2700 mg per day to about 3000 mg per day, from about 2800 mg per day to about 3000 mg per day, from about 2900 mg per day to about 3000 mg per day, from about 50 mg per day to about 2800 mg per day, from about 100 mg per day to about 2800 mg per day, from about 150 mg per day to about 2800 mg per day, from about 200 mg per day to about 2800 mg per day, from about 300 mg per day to about 2800 mg per day, from about 400 mg per day to about 2800 mg per day, from about 500 mg per day to about 2800 mg per day, from about 600 mg per day to about 2800 mg per day, from about 700 mg per day to about 2800 mg per day, from about 800 mg per day to about 2800 mg per day, from about 900 mg per day to about 2800 mg per day, from about 1000 mg per day to about 2800 mg per day, from about 1100 mg per day to about 2800 mg per day, from about 1200 mg per day to about 2800 mg per day, from about 1300 mg per day to about 2800 mg per day, from about 1400 mg per day to about 2800 mg per day, from about 1500 mg per day to about 2800 mg per day, from about 1600 mg per day to about 2800 mg per day, from about 1700 mg per day to about 2800 mg per day, from about 1800 mg per day to about 2800 mg per day, from about 1900 mg per day to about 2800 mg per day, from about 2000 mg per day to about 2800 mg per day, from about 2100 mg per day to about 2800 mg per day, from about 2200 mg per day to about 2800 mg per day, from about 2300 mg per day to about 2800 mg per day, from about 2400 mg per day to about 2800 mg per day, from about 2500 mg per day to about 2800 mg per day, from about 2600 mg per day to about 2800 mg per day, from about 2700 mg per day to about 2800 mg per day, from about 50 mg per day to about 2500 mg per day, from about 100 mg per day to about 2500 mg per day, from about 150 mg per day to about 2500 mg per day, from about 200 mg per day to about 2500 mg per day, from about 300 mg per day to about 2500 mg per day, from about 400 mg per day to about 2500 mg per day, from about 500 mg per day to about 2500 mg per day, from about 600 mg per day to about 2500 mg per day, from about 700 mg per day to about 2500 mg per day, from about 800 mg per day to about 2500 mg per day, from about 900 mg per day to about 2500 mg per day, from about 1000 mg per day to about 2500 mg per day, from about 1100 mg per day to about 2500 mg per day, from about 1200 mg per day to about 2500 mg per day, from about 1300 mg per day to about 2500 mg per day, from about 1400 mg per day to about 2500 mg per day, from about 1500 mg per day to about 2500 mg per day, from about 1600 mg per day to about 2500 mg per day, from about 1700 mg per day to about 2500 mg per day, from about 1800 mg per day to about 2500 mg per day, from about 1900 mg per day to about 2500 mg per day, from about 2000 mg per day to about 2500 mg per day, from about 2100 mg per day to about 2500 mg per day, from about 2200 mg per day to about 2500 mg per day, from about 2300 mg per day to about 2500 mg per day, from about 2400 mg per day to about 2500 mg per day, from about 50 mg per day to about 2200 mg per day, from about 100 mg per day to about 2200 mg per day, from about 150 mg per day to about 2200 mg per day, from about 200 mg per day to about 2200 mg per day, from about 300 mg per day to about 2200 mg per day, from about 400 mg per day to about 2200 mg per day, from about 500 mg per day to about 2200 mg per day, from about 600 mg per day to about 2200 mg per day, from about 700 mg per day to about 2200 mg per day, from about 800 mg per day to about 2200 mg per day, from about 900 mg per day to about 2200 mg per day, from about 1000 mg per day to about 2200 mg per day, from about 1100 mg per day to about 2200 mg per day, from about 1200 mg per day to about 2200 mg per day, from about 1300 mg per day to about 2200 mg per day, from about 1400 mg per day to about 2200 mg per day, from about 1500 mg per day to about 2200 mg per day, from about 1600 mg per day to about 2200 mg per day, from about 1700 mg per day to about 2200 mg per day, from about 1800 mg per day to about 2200 mg per day, from about 1900 mg per day to about 2200 mg per day, from about 2000 mg per day to about 2200 mg per day, from about 2100 mg per day to about 2200 mg per day, from about 50 mg per day to about 2000 mg per day, from about 100 mg per day to about 2000 mg per day, from about 150 mg per day to about 2000 mg per day, from about 200 mg per day to about 2000 mg per day, from about 300 mg per day to about 2000 mg per day, from about 400 mg per day to about 2000 mg per day, from about 500 mg per day to about 2000 mg per day, from about 600 mg per day to about 2000 mg per day, from about 700 mg per day to about 2000 mg per day, from about 800 mg per day to about 2000 mg per day, from about 900 mg per day to about 2000 mg per day, from about 1000 mg per day to about 2000 mg per day, from about 1100 mg per day to about 2000 mg per day, from about 1200 mg per day to about 2000 mg per day, from about 1300 mg per day to about 2000 mg per day, from about 1400 mg per day to about 2000 mg per day, from about 1500 mg per day to about 2000 mg per day, from about 1600 mg per day to about 2000 mg per day, from about 1700 mg per day to about 2000 mg per day, from about 1800 mg per day to about 2000 mg per day, from about 1900 mg per day to about 2000 mg per day, from about 50 mg per day to about 1800 mg per day, from about 100 mg per day to about 1800 mg per day, from about 150 mg per day to about 1800 mg per day, from about 200 mg per day to about 1800 mg per day, from about 300 mg per day to about 1800 mg per day, from about 400 mg per day to about 1800 mg per day, from about 500 mg per day to about 1800 mg per day, from about 600 mg per day to about 1800 mg per day, from about 700 mg per day to about 1800 mg per day, from about 800 mg per day to about 1800 mg per day, from about 900 mg per day to about 1800 mg per day, from about 1000 mg per day to about 1800 mg per day, from about 1100 mg per day to about 1800 mg per day, from about 1200 mg per day to about 1800 mg per day, from about 1300 mg per day to about 1800 mg per day, from about 1400 mg per day to about 1800 mg per day, from about 1500 mg per day to about 1800 mg per day, from about 1600 mg per day to about 1800 mg per day, from about 1700 mg per day to about 1800 mg per day, from about 50 mg per day to about 1500 mg per day, from about 100 mg per day to about 1500 mg per day, from about 150 mg per day to about 1500 mg per day, from about 200 mg per day to about 1500 mg per day, from about 300 mg per day to about 1500 mg per day, from about 400 mg per day to about 1500 mg per day, from about 500 mg per day to about 1500 mg per day, from about 600 mg per day to about 1500 mg per day, from about 700 mg per day to about 1500 mg per day, from about 800 mg per day to about 1500 mg per day, from about 900 mg per day to about 1500 mg per day, from about 1000 mg per day to about 1500 mg per day, from about 1100 mg per day to about 1500 mg per day, from about 1200 mg per day to about 1500 mg per day, from about 1300 mg per day to about 1500 mg per day, from about 1400 mg per day to about 1500 mg per day, from about 50 mg per day to about 1200 mg per day, from about 100 mg per day to about 1200 mg per day, from about 150 mg per day to about 1200 mg per day, from about 200 mg per day to about 1200 mg per day, from about 300 mg per day to about 1200 mg per day, from about 400 mg per day to about 1200 mg per day, from about 500 mg per day to about 1200 mg per day, from about 600 mg per day to about 1200 mg per day, from about 700 mg per day to about 1200 mg per day, from about 800 mg per day to about 1200 mg per day, from about 900 mg per day to about 1200 mg per day, from about 1000 mg per day to about 1200 mg per day, from about 1100 mg per day to about 1200 mg per day, from about 50 mg per day to about 1000 mg per day, from about 100 mg per day to about 1000 mg per day, from about 150 mg per day to about 1000 mg per day, from about 200 mg per day to about 1000 mg per day, from about 300 mg per day to about 1000 mg per day, from about 400 mg per day to about 1000 mg per day, from about 500 mg per day to about 1000 mg per day, from about 600 mg per day to about 1000 mg per day, from about 700 mg per day to about 1000 mg per day, from about 800 mg per day to about 1000 mg per day, from about 900 mg per day to about 1000 mg per day, from about 50 mg per day to about 800 mg per day, from about 100 mg per day to about 800 mg per day, from about 150 mg per day to about 800 mg per day, from about 200 mg per day to about 800 mg per day, from about 300 mg per day to about 800 mg per day, from about 400 mg per day to about 800 mg per day, from about 500 mg per day to about 800 mg per day, from about 600 mg per day to about 800 mg per day, from about 700 mg per day to about 800 mg per day, from about 50 mg per day to about 600 mg per day, from about 100 mg per day to about 600 mg per day, from about 150 mg per day to about 600 mg per day, from about 200 mg per day to about 600 mg per day, from about 300 mg per day to about 600 mg per day, from about 400 mg per day to about 600 mg per day, from about 500 mg per day to about 600 mg per day, from about 50 mg per day to about 500 mg per day, from about 100 mg per day to about 500 mg per day, from about 150 mg per day to about 500 mg per day, from about 200 mg per day to about 500 mg per day, from about 300 mg per day to about 500 mg per day, from about 400 mg per day to about 500 mg per day, from about 50 mg per day to about 400 mg per day, from about 100 mg per day to about 300 mg per day, from about 100 mg per day to about 200 mg per day, from about 200 mg per day to about 500 mg per day, from about 300 mg per day to about 500 mg per day, or from about 400 mg per day to about 500 mg per day.

In some embodiments, the oral dose is about 10 mg per day, about 15 mg per day, about 20 mg per day, about 30 mg per day, about 40 mg per day, about 50 mg per day, about 100 mg per day, about 150 mg per day, about 200 mg per day, about 250 mg per day, about 300 mg per day, about 350 mg per day, about 400 mg per day, about 450 mg per day, about 500 mg per day, about 550 mg per day, about 600 mg per day, about 650 mg per day, about 700 mg per day, about 750 mg per day, about 800 mg per day, about 850 mg per day, about 900 mg per day, about 950 mg per day, about 1000 mg per day, about 1100 mg per day, about 1200 mg per day, about 1300 mg per day, about 1400 mg per day, about 1500 mg per day, about 1600 mg per day, about 1700 mg per day, about 1800 mg per day, about 1900 mg per day, about 2000 mg per day, about 2100 mg per day, about 2200 mg per day, about 2300 mg per day, about 2400 mg per day, about 2500 mg per day, about 2600 mg per day, about 2700 mg per day, about 2800 mg per day, about 2900 mg per day, or about 3000 mg per day.

In some embodiments, trapidil, a derivative, a metabolite, a prodrug, an analog, or a pharmaceutically acceptable salt thereof is administered in a single dose. In some embodiments, trapidil, a derivative, a metabolite, a prodrug, an analog, or a pharmaceutically acceptable salt thereof is administered in several doses, e.g., in 2, 3, 4, 5, 6, or more doses per day. In some embodiments, trapidil, a derivative, a metabolite, a prodrug, an analog, or a pharmaceutically acceptable salt thereof is administered intravenously or subcutaneously. In such instances, the intravenous or subcutaneous administration dose ranges from about 1 mg/kg body weight to about 10 mg/kg body weight, from about 2 mg/kg body weight to about 10 mg/kg body weight, or from about 4 mg/kg body weight to about 8 mg/kg body weight.

2. Combination Therapies

Disclosed herein, in certain embodiments, are methods of treating or preventing a cognitive disorder in a subject in need thereof comprising administering to the subject a therapeutically effective dose of trapidil, a derivative, a metabolite, a prodrug, an analog, or a pharmaceutically acceptable salt thereof; and an additional therapeutic agent. In some embodiments, the additional therapeutic agent is administered simultaneously with the trapidil, the derivative, the metabolite, the prodrug, the analog, or the pharmaceutically acceptable salt thereof. In some embodiments, the additional therapeutic agent is administered before or after the trapidil, the derivative, the metabolite, the prodrug, the analog, or the pharmaceutically acceptable salt thereof. In some embodiments, the combination of trapidil and the additional therapeutic agent is therapeutically effective to treat or prevent the cognitive disorder or psychological condition in a subject in need thereof.

In some embodiments, the administration of the trapidil, the derivative, the metabolite, the prodrug, the analog, or the pharmaceutically acceptable salt thereof, potentiates the additional therapeutic agent such that a subclinical dose of the additional therapeutic is needed to treat the cognitive disorder or the psychological condition. In some embodiments, the additional therapeutic is levodopa.

In some embodiments, the additional therapeutic agent comprises an antidepressant. Non-limiting examples of antidepressants include: citalopram (Celexa), escitalopram (Lexapro), fluoxetine (Prozac, Sarafem, Selfemra, Prozac Weekly), fluvoxamine (Luvox), paroxetine (Paxil, Paxil CR, Pexeva), sertraline (Zoloft), vortioxetine (Trintellix, formerly known as Brintellix), and vilazodone (Viibryd). In some embodiments, trapidil, a derivative, a metabolite, a prodrug, an analog, or a pharmaceutically acceptable salt thereof is administered in combination with an antidepressant.

In some embodiments, the additional therapeutic agent comprises an antipsychotic medication. Non-limiting examples of antipsychotic medications include: aripiprazole (Abilify), asenapine (Saphris), cariprazine (Vraylar), clozapine (Clozaril), lurasidone (Latuda), olanzapine (Zyprexa), quetiapine (Seroquel), risperidone (Risperdal), and ziprasidone (Geodon). In some embodiments, the antipsychotic medication comprises chlorpromazine, fluphenazine, haloperidol, perphenazine, or any combination thereof. In some embodiments, trapidil, a derivative, a metabolite, a prodrug, an analog, or a pharmaceutically acceptable salt thereof is administered in combination with an antipsychotic medication.

In some embodiments, the additional therapeutic agent comprises an anxiolytic medication. Non-limiting examples of anxiolytic medication include: alprazolam (Xanax), chlordiazepoxide (Librium), clonazepam (Klonopin), diazepam (Valium), and lorazepam (Ativan). In some embodiments, trapidil, a derivative, a metabolite, a prodrug, an analog, or a pharmaceutically acceptable salt thereof is administered in combination with an anxiolytic medication.

In some embodiments, the additional therapeutic agent comprises a dopamine precursor or a dopamine agonist. In some embodiments, trapidil, a derivative, a metabolite, a prodrug, an analog, or a pharmaceutically acceptable salt thereof is administered in combination with a dopamine precursor. In some embodiments, trapidil, a derivative, a metabolite, a prodrug, an analog, or a pharmaceutically acceptable salt thereof is administered in combination with a dopamine agonist.

In some embodiments, the dopamine precursor comprises levodopa. In some embodiments, the dopamine precursor is a combination of levodopa and carbidopa. In some embodiments, the dopamine precursor is a combination of levodopa and benserazide. In some embodiments, trapidil, the derivative, the metabolite, the prodrug, the analog, or the pharmaceutically acceptable salt thereof is administered in combination with levodopa and/or carbidopa. In some embodiments, trapidil, the derivative, the metabolite, the prodrug, the analog, or the pharmaceutically acceptable salt thereof is administered in combination with levodopa and/or benserazide.

In some embodiments, the additional therapeutic agent is a dopamine agonist comprising pramipexole, ropinirole, rotigotine, pergolide, bromocriptine, piribedile, bromocriptine, lisuride, apomorphine, levodopa, entacapone, selegiline, rasagiline, and/or tolcapone. In some embodiments, trapidil, the derivative, the metabolite, the prodrug, the analog, or the pharmaceutically acceptable salt thereof is administered in combination with pramipexole, ropinirole, rotigotine, pergolide, bromocriptine, piribedile, bromocriptine, lisuride, apomorphine, levodopa, entacapone, selegiline, rasagiline, and/or tolcapone.

In some embodiments, the additional therapeutic agent alone, or in combination with trapidil, is administered orally. In some embodiments, the additional therapeutic agent alone, or in combination with trapidil, is administered intravenously or subcutaneously.

In some embodiments, trapidil, a derivative, a metabolite, a prodrug, an analog, or a pharmaceutically acceptable salt thereof and the additional therapeutic agent are administered simultaneously. In some embodiments, trapidil, a derivative, a metabolite, a prodrug, an analog, or a pharmaceutically acceptable salt thereof and the additional therapeutic agent are administered sequentially. In some embodiments, trapidil, a derivative, a metabolite, a prodrug, an analog, or a pharmaceutically acceptable salt thereof is administered before the additional therapeutic agent. In some embodiments, trapidil, a derivative, a metabolite, a prodrug, an analog, or a pharmaceutically acceptable salt thereof is administered after the additional therapeutic agent. In some embodiments, trapidil, a derivative, a metabolite, a prodrug, an analog, or a pharmaceutically acceptable salt thereof and the additional therapeutic agent are administered in a unified dosage form. In some embodiments, trapidil, a derivative, a metabolite, a prodrug, an analog, or a pharmaceutically acceptable salt thereof and the additional therapeutic agent are administered in separate dosage forms.

D. Therapeutic Regimen

In some embodiments, the therapeutic agent, combination therapies, or pharmaceutical compositions described herein are administered according to a particular regimen. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In some embodiments, trapidil and an additional therapeutic agent are administered simultaneously, sequentially, or at an interval period of time. In some embodiments, trapidil and an additional therapeutic agent are administered simultaneously. In some embodiments, trapidil and an additional therapeutic agent are administered sequentially. In additional cases, trapidil and an additional therapeutic agent are administered at an interval period of time (e.g., the first administration of a first pharmaceutical composition (e.g., trapidil) is on day one followed by an interval of at least 1, 2, 3, 4, 5, or more days prior to the administration of at least a second pharmaceutical composition (e.g., an additional therapeutic agent).

In the case wherein the patient's status does improve, upon the doctor's discretion the administration of the composition is given continuously; alternatively, the dose of the composition being administered is temporarily reduced or temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions (e.g., cognitive impairment or disorder) has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some embodiments, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

II. COMPOSITIONS AND FORMULATIONS

Disclosed herein, in some embodiments, are pharmaceutical compositions (or combinations) comprising a therapeutic agent disclosed herein. In some embodiments, the pharmaceutical composition comprises trapidil, a derivative, a metabolite, a prodrug, an analog, or a pharmaceutically acceptable salt thereof. In some embodiments, the pharmaceutical composition, or combination, further comprises an additional therapeutic agent. In some embodiments, the additional therapeutic agent is a dopamine precursor (e.g., levodopa). In some embodiments, the additional therapeutic agent is a combination therapy of a dopamine precursor (e.g., levodopa) and adjunctive therapy (e.g., carbidopa). In some embodiments, the additional therapeutic agent is a dopamine agonist (e.g., rotigotine, cabergoline, pergolide, bromocriptine, piribedil, pramipexole, ropinirole, lisuride, quinagolide, or apomorphine). In some embodiments, the pharmaceutical composition or combination is therapeutically effective to treat or prevent the cognitive disorder or the psychological condition in the subject. In some embodiments, the pharmaceutical composition or combination further comprises at least one pharmaceutically acceptable: excipient, carrier, or diluent. In some embodiments, the pharmaceutical combination is in a fixed-dosage combination. In some embodiments, the dosage amount of trapidil in the pharmaceutical composition or combination is less than or equal to about 200 milligrams.

A. Pharmaceutical Compositions and Formulations

Disclosed herein, in certain embodiments, are pharmaceutical compositions or combinations which comprise a therapeutic agent described herein. In some embodiments, the therapeutic agent is trapidil. In some embodiments, the pharmaceutical composition further comprises an additional therapeutic agent. In some embodiments, the additional therapeutic agent is a dopamine precursor (e.g., levodopa) or a dopamine agonist. In some embodiments, pharmaceutical compositions or combinations are formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients are used as suitable and as understood in the art. A summary of pharmaceutical compositions described herein are found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, New York, 1980; and *Pharmaceutical Dosage Forms and Drug Delivery Systems*, Seventh Ed. (Lippincott Williams & Wilkins 1999), herein incorporated by reference in their entirety A pharmaceutical composition, as used herein, refers to a mixture of a compound described herein, such as, for example, trapidil and an additional therapeutic agent for treating Parkinson's disease, with other chemical components, such as carriers, stabilizers, diluents, dispersing agents, suspending agents, thickening agents, and/or excipients. The pharmaceutical composition or combination facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions or combinations also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions or combinations also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, pharmaceutical compositions including a compound described herein are manufactured in a conventional manner, such as, by way of example only, by means of conventional mixing, dissolving, granulating, dragee-making, levigating, emulsifying, encapsulating, entrapping or compression processes.

In some embodiments, "antifoaming agents" reduce foaming during processing which result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In additional embodiments, formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

B. Dosage Forms

In some embodiments, the compositions or combinations described herein are formulated for administration to a subject via any conventional means including, but not limited to, oral, parenteral (e.g., intravenous, subcutaneous, or intramuscular), buccal, intranasal, rectal or transdermal administration routes. In some embodiments, the composition is formulated for administration in a combined dosage form. In some embodiments, the composition is formulated for administration in a separate dosage forms.

Moreover, the pharmaceutical compositions described herein, which include trapidil and an additional therapeutic agent are formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions are used, which optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments are added to the tablets or dragee coatings for identification or to characterize different combinations of active compound doses.

Pharmaceutical preparations which are used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of trapidil and/or an additional therapeutic agent, with one or more pharmaceutical excipients to form a bulk blend composition. When referring to these bulk blend compositions as homogeneous, it is meant that the particles of trapidil and/or an additional therapeutic agent, are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

In some embodiments, the pharmaceutical solid dosage forms described herein include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences,* 20th Edition (2000), a film coating is provided around the formulation of trapidil and/or an additional therapeutic agent. In another embodiment, some or all of the particles of trapidil and/or an additional therapeutic agent, are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of trapidil and/or an additional therapeutic agent, from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of trapidil and/or an additional therapeutic agent, from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule is prepared, for example, by placing the bulk blend of the formulation of trapidil and/or an additional therapeutic agent, described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of trapidil and/or an additional therapeutic agent, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with trapidil and/or an additional therapeutic agent, which sufficiently isolate the compound of any of trapidil or an additional therapeutic agent, from other non-compatible excipients. Materials compatible with compounds of any of trapidil or an additional therapeutic agent, are those that delay the release of the compounds of any of trapidil or an additional therapeutic agent, in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG,HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of any of trapidil or an additional therapeutic agent, may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In other embodiments, the solid dosage formulations of the compounds of any of trapidil and/or an additional therapeutic agent, are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound of any of trapidil and/or an additional therapeutic agent, described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles <1 μm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include trapidil and/or an additional therapeutic agent, are delivered using a pulsatile dosage form. A pulsatile dosage form is capable of providing one or more immediate release pulses at predetermined time points after a controlled lag time or at specific sites. Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms,* 2 Ed., Vol. 1, pp. 209-214 (1990); Singh et al., *Encyclopedia of Pharmaceutical Technology,* $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

In some embodiments, pharmaceutical formulations are provided that include particles of trapidil and/or an additional therapeutic agent, described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology,* $2^{nd}$ Ed., pp. 754-757 (2002). In addition, the liquid dosage forms may include additives, such as: (a) disintegrating agents; (b) dispersing agents; (c) wetting agents; (d) at least one preservative, (e) viscosity enhancing agents, (0 at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

1. Injectable Formulations

Formulations that include a compound of trapidil or an additional therapeutic agent, suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

2. Additional Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

In some embodiments, the compounds described herein are also formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

III. DEFINITIONS

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed.

In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include," "includes," and "included," is not limiting.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error.

The section headings used herein are for organizational purposes only and are not to be construed as limiting the subject matter described.

As used herein, "drug", "pharmaceutical", "small-molecule drug", "biologic drug", "biopharmaceutical", and "therapeutic", are used interchangeably to refer to an exogenous compound administered to a patient for a therapeutic purpose. These compounds are obtained by the patient either with a prescription from a medical professional or without a prescription for over the counter items.

As used herein, a "cognitive disorder" refers to a condition that affects cognitive ability that may have an underlying brain pathology. In some embodiments, cognitive impairment is a single disease, symptom, sign, or diagnosis. In some embodiments, cognitive impairment is a set of closely related diseases, symptoms, signs, or diagnoses.

As used herein, a "cognitive impairment," refers to a cognitive disorder that causes a decline or deficit in cognition. In some embodiments, the cognitive impairment comprises a decline or deficit one or more of the five cognitive domains, including: attention, working memory, executive function, visuospatial function, and memory.

As used herein, "cognition" refers to mental action including, for example, working memory, executive function, visuospatial function, memory, association, concept formation, pattern recognition, language, attention, perception, action, problem solving, and mental imagery.

As used herein, a "derivative" refers to compounds that are derived from or obtained from a compound disclosed herein. In some embodiments, a derivative improves its solubility, absorption, biological half-life, and the like, or decreases the toxicity of the molecule, eliminate or attenuate any undesirable side effect of the molecule, and the like.

In some embodiments, a derivative of a compound described herein include a an isotopically labeled compound (e.g., with a radioisotope) or by another means, including, but not limited to, the use of chromophores or fluorescent moieties, bioluminescent labels, or chemiluminescent labels. Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that are incorporated into the present compounds include isotopes of hydrogen, carbon, nitrogen, oxygen, fluorine and chlorine, such as, for example, 2H, 3H, 13C, 14C, 15N, 18O, 17O, 35S, 18F, 36Cl. In some embodiments, isotopically-labeled compounds described herein, for example those into which radioactive isotopes such as 3H and 14C are incorporated, are useful in drug and/or substrate tissue distribution assays.

In some embodiments, a derivative of a compound described herein is a deuterated version of the compound. In some embodiments, a deuterated version of the compound comprises at least one, two, three, four, five, six, seven, eight, nine, ten, or more deuterium substitutions. In some embodiments, substitution with isotopes such as deuterium affords certain therapeutic advantages resulting from greater metabolic stability, such as, for example, increased in vivo half-life or reduced dosage requirements.

In some embodiments, a derivative of a compound described herein comprises AR 12455, AR 12456, AR 12460, AR 12463, AR 12464, AR 12465, or AR 12565.

As used herein, a "metabolite" of a compound disclosed herein refers to the intermediates and products of that compound that is formed when the compound is metabolized. In additional embodiments, compounds described herein are metabolized upon administration to an organism in need to produce a metabolite that is then used to produce a desired effect, including a desired therapeutic effect. In some embodiments, a metabolite of a compound disclosed herein is an active metabolite. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, In some embodiments, enzymes produce specific structural alterations to a compound.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In some embodiments, exemplary metabolites disclosed herein include, but are not limited to, desethyl-trapidil, 5-piperidin-4'-olyl-7-[N-pentyl-N-(beta-hydroxyethyl)] amino-s-triazolo[1,5-a]pyrimidine, 5-piperidin-4'-olyl-7-[N-pent-4-olyl-N-(beta-hydroxyethyl)]amino-s-triazolo[1,5-a]pyrimidine, hydroxy- or ketopentyl derivatives, piperidinoles or piperidinones, TP1, or TP2.

In some embodiments, metabolites of the compounds disclosed herein are optionally identified either by administration of compounds to a host and analysis of tissue samples from the host, or by incubation of compounds with hepatic cells in vitro and analysis of the resulting compounds.

As used herein, a "prodrug" of a compound disclosed herein refers to an agent that is converted into the compound disclosed herein in vivo. Prodrugs are often useful because, in some situations, they are easier to administer than the parent drug. In some embodiments, prodrugs are bioavailable by oral administration whereas the parent is not. In some embodiments, the prodrugs have improved solubility in pharmaceutical compositions over the parent drug. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In some embodiments, the prodrug is designed to alter the metabolic stability or the transport characteristics of a drug, to mask side effects or toxicity, to improve the flavor of a drug or to alter other characteristics or properties of a drug. In some embodiments, prodrugs are designed as reversible drug derivatives, for use as modifiers to enhance drug transport to site-specific tissues. By virtue of knowledge of pharmacodynamic processes and drug metabolism in vivo, those of skill in this art, once a pharmaceutically active compound is known, can design prodrugs of the compound. (see, for example, Nogrady (1985) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Saulnier et al., (1994), Bioorganic and Medicinal Chemistry Letters, Vol. 4, p. 1985).

As used herein, an "analog" refers to compounds that are structurally and functionally similar to, or mimics the effects of, a compound disclosed herein. In some embodiments, an analog mimics the biological effect of a compound disclosed herein. In other instances, an analog mimics the physical effect of a compound disclosed herein.

As used herein, a "pharmaceutically acceptable salt" refers to salts of the compound disclosed herein that have no persistent detrimental effect on the general health of the subject being treated or does not abrogate the biological activity or properties of the compound, and is relatively non-toxic. In some embodiments, a "pharmaceutically acceptable salt" includes a salt with an inorganic base, organic base, inorganic acid, organic acid, or basic or acidic amino acid. Salts of inorganic bases include, for example, alkali metals such as sodium or potassium; alkaline earth metals such as calcium and magnesium or aluminum; and ammonia. Salts of organic bases include, for example, trimethylamine, triethylamine, pyridine, picoline, ethanolamine, diethanolamine, and triethanolamine. Salts of inorganic acids include for example, hydrochloric acid, hydroboric acid, nitric acid, sulfuric acid, and phosphoric acid. Salts of organic acids include for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Salts of basic amino acids include, for example, arginine, lysine and ornithine. Acidic amino acids include, for example, aspartic acid and glutamic acid.

As used herein, a "psychological condition" refers to a condition that affects mood, thinking, behavior, or a combination thereof. In some embodiments, a psychological condition comprises clinical depression, anxiety, apathy, or lack of motivation. In some embodiments, the psychological condition is psychosis.

As used herein, "Parkinson's disease" refers to a disease of the brain that affects motor function. Notable symptoms of Parkinson's disease include (i) tremor in the hands, arms, legs, jaw or head, (ii) stiffness of the limbs and trunk, (iii) slowness of movement, and (iv) impaired balance and coordination.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds described herein, as well as active metabolites of these compounds having the same type of activity.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of trapidil and an additional therapeutic agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, μg, or ng of therapeutic agent per mL, dL, or L of blood serum, absorbed into the bloodstream after administration. As used herein, measurable plasma concentrations are typically measured in ng/ml or μg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

IV. EXAMPLES

The following examples are included for illustrative purposes only and are not intended to limit the scope of the invention.

Example 1: Single Cell Deconvolution of Trapidil Effects in Bulk Striatum of Parkinsonian Rats Demonstrates Modulation of Neurons Expression Dopamine 1 Receptors Sprague Dawley male rats (n=25) were rendered Parkinsonian through administration of 6-hydroxydopamine ("6-OHDA") into the medial forebrain bundle unilaterally. After recovery from surgery for two weeks, the rats were split into three groups and received intraperitoneally daily for two weeks either 1) levodopa (6 mg/kg)/benserazide (15 mg/kg) and vehicle (BID) (n=5), 2) levodopa (6 mg/kg)/benserazide (15 mg/kg) and trapidil (7.5 mg/kg, BID) (n=10), or 3) levodopa (6 mg/kg)/benserazide (15 mg/kg) and trapidil (15 mg/kg, BID) (n=10). On Day 14, after last drug administration, rats were sacrificed and striatum ipsilateral to the lesion was collected. RNA was extracted from bulk tissue. Preparatory steps were completed for RNA-seq on Illumina sequencers. Samples were sequenced to roughly 28 million reads per sample on average. After quality control steps, reads for each sample were aligned (using STAR) to the *Rattus norvegicus* genome, counted (using HTseq), and differential expression was calculated (using DESeq2).

Bulk tissue RNA-seq results were computationally deconvoluted into predicted effects on individual cell types using a recently developed algorithm (Frishberg et al. Nature Methods 2019) and single cell RNA-seq reference data from mouse striatum (Gokce et al. Cell Reports 2016). By deconvoluting the bulk tissue data into 11 cell types (including neurons expressing dopamine 1 receptor or dopamine 2 receptors, astrocytes, oligodendrocytes, immune cells, and vascular cells), it was assessed which cell types had gene expression changes due to trapidil. The only cell type's expression that was significantly activated by trapidil were neurons expressing dopamine 1 receptors (FIG. 1). Such changes in expression of neurons expressing dopamine 1 receptors is consistent with dopamine agonists that activate dopamine 1 receptors (Gerfen et al. Science 1990). This finding is surprising as trapidil is not an activator or inhibitor of dopamine receptors (Example 2).

As cognitive impairment in Parkinson's disease may be due to deficits in dopaminergic signaling, trapidil may be therapeutically useful.

Example 2: Trapidil does not Activate, Inhibit, or Modulate Dopamine Receptors

Figure 2:
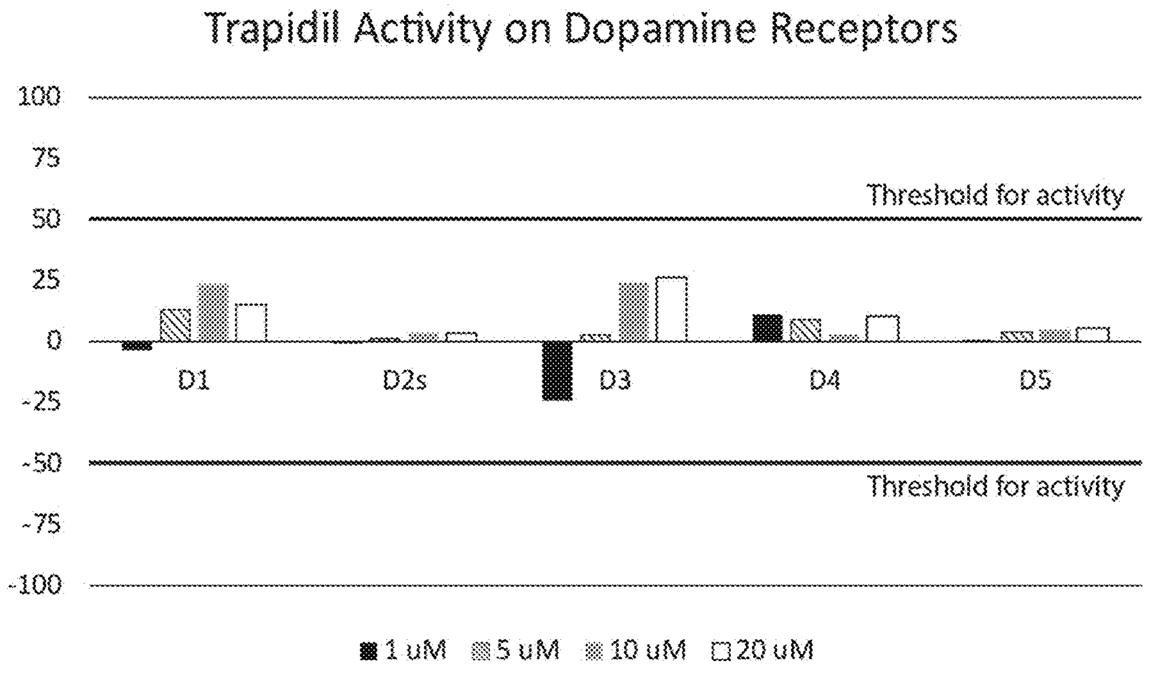
FIG. 2 exemplifies trapidil's inability to activate, inhibit, or modulate dopamine receptors (D1, D2s, D3, D4, and D5).

Trapidil was tested on cell-based pharmacological assays at relevant physiological concentrations (up to 20 uM) for dopamine receptors (D1, D2s, D3, D4, and D5). No significant effects (threshold set at 50% activation or inhibition) were seen at any of the four concentrations used (FIG. 2).

Example 3: Initial Dosing Levels of Trapidil for Non-Human Primate Testing

Efficacy studies often generate un-interpretable data because of incorrect dosing. Although the human and rat plasma PK profiles of SB-0107 are available, the dose-exposure relationship of trapidil in non-human primates is not available. Plasma levels of oral dosing of trapidil were characterized in MPTP lesioned Parkinsonian non-human primates at four different doses: 3, 10, 15, and 20 mg/kg. Blood was collected before and after administration of drug compound (10 min, 30 min, 1 h, 2 h, 4 h, 6 h, 8 h, and 24 h) for analysis. Calculated pharmacokinetic parameters are shown in Table 1. Ultimately, oral doses of 10 and 15 mg/kg were used for efficacy studies (Example 4).

TABLE 1

Pharmacokinetic parameters of oral doses of trapidil in non-human primates. Average of n = 3 (Standard deviation in parentheses)

| trapidil Dose | 3 mg/kg | 10 mg/kg | 15 mg/kg | 20 mg/kg |
|---|---|---|---|---|
| Cmax (ng/mL) | 252 (42) | 1560 (11.5) | 4940 (1230) | 7930 (1510) |
| AUC (ug/mL*h) | 0.261 (0.038) | 1.88 (0.65) | 6.31 (1.45) | 11.5 (4.87) |
| Tmax (h) | 0.334 (0.235) | 0.667 (0.289) | 0.667 (0.289) | 0.722 (0.481) |
| Half life (h) | 0.445 (0.082) | 0.503 (0.099) | 0.568 (0.135) | 0.451 (0.0417) |

Example 4: Efficacy of Trapidil in Treating Cognitive Impairment in the Chronic Low Dose MPTP Lesioned Non-Human Primate Model Using dosages determined from Example 3, trapidil was administered to test in vivo efficacy for treatment in the chronic low-dose MPTP lesioned non-human primate model of cognitive impairment in Parkinson's disease.

Animals develop mild cognitive impairment due to chronic low-doses of the toxin MPTP, but do not develop motor impairment, allowing for assessing cognitive dysfunctions in the same areas seen in patients, including attention, working memory, and executive function. trapidil's ability to enhance cognitive tests with or without low-dose levodopa (which has minimal effect on cognitive function) are tested and compared to higher doses of levodopa (which begins to impair cognitive function).

Five male non-human primates are used and received eight treatments in a randomized partial Latin-square design (Table 2). The animals have been previously trained to complete several cognitive tasks before lesioning, including variable delayed response (VDR). VDR is a spatial working memory task where an NHP is rewarded for remembering a location on a screen after a variable delay period (between 2-60 seconds, DP1-DP5). Shorter periods (i.e. DP1, DP2) only require an attentional component while longer delay periods have an additional memory component (i.e. D4, D5). This task was specifically chosen due to its cognitive domain (spatial working memory and attention), because these tasks are improved by dopamine 1 receptor agonism in cognitive impairment models, and high doses of levodopa impair these tasks in the model and impairs cognitive function in Parkinson's disease patients.

TABLE 2

Treatments for assessing pro-cognitive effects of trapidil in a primate model of cognitive deficits in Parkinson's disease.

| Treatment # | Treatment A | Treatment B |
|---|---|---|
| 1 | Vehicle | Vehicle |
| 2 | Vehicle | trapidil (10 mg/kg) |
| 3 | Vehicle | trapidil (15 mg/kg) |
| 4 | Levodopa (5 mg/kg) | trapidil (10 mg/kg) |
| 5 | Levodopa (5 mg/kg) | trapidil (15 mg/kg) |
| 6 | Levodopa (5 mg/kg) | Vehicle |
| 7 | Levodopa (10 mg/kg) | Vehicle |
| 8 | Levodopa (20 mg/kg) | Vehicle |

Figure 3:
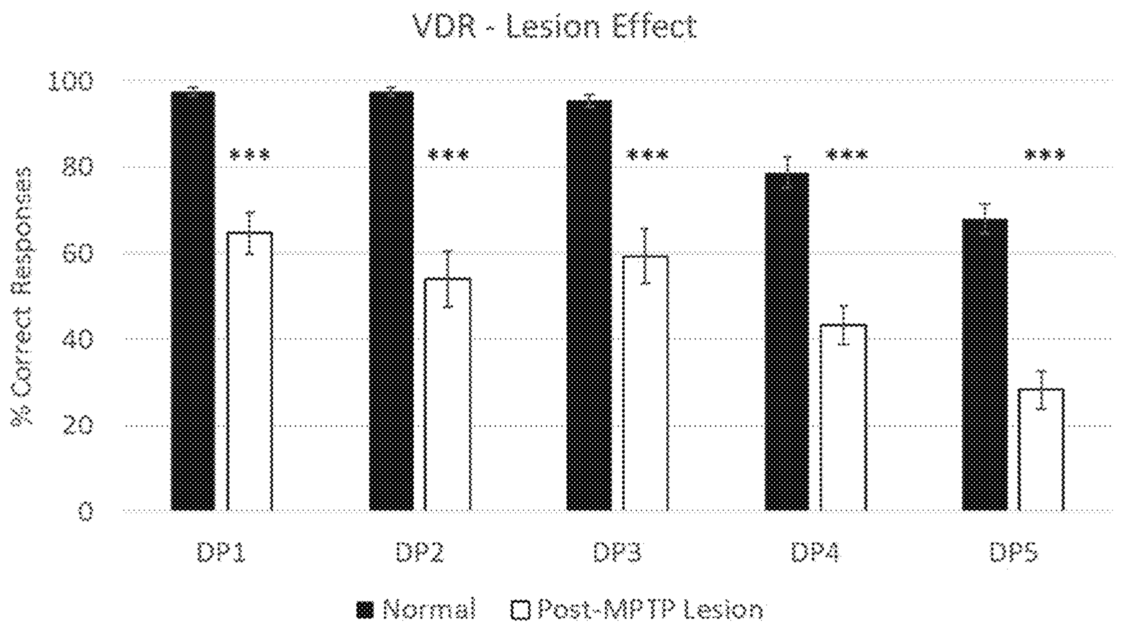
FIG. 3 exemplifies that the variable delayed response (VDR) task can delineate between normal primates and primates after chronic low dose MPTP, providing a model of cognitive deficits in Parkinson's disease. Compared to normal: ***p<0.01
Figure 4:
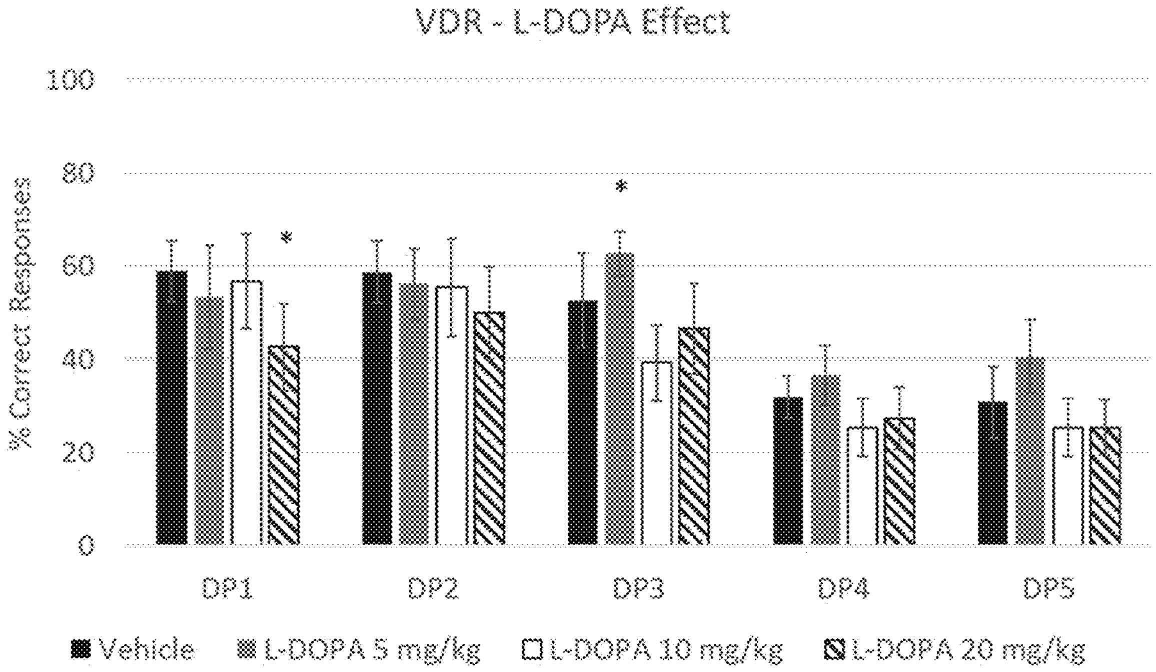
FIG. 4 exemplifies that the treatment of MPTP lesioned primates with levodopa trends toward decreasing ability in accurately completing the VDR task. Compared to vehicle: *p<0.1

After chronic low-dose MPTP, the five primates exhibit significant deficits in their ability to accurately complete the VDR task at all five delay periods (FIG. 3), thus demonstrating cognitive deficits in the domains of spatial working memory, executive function, and attention. When the animals are dosed with levodopa (5-20 mg/kg, groups 6-8), they trend toward completing the VDR test with lower accuracy (FIG. 4), in particular for the shorter delay periods (DP1 and DP2).

Figure 5:
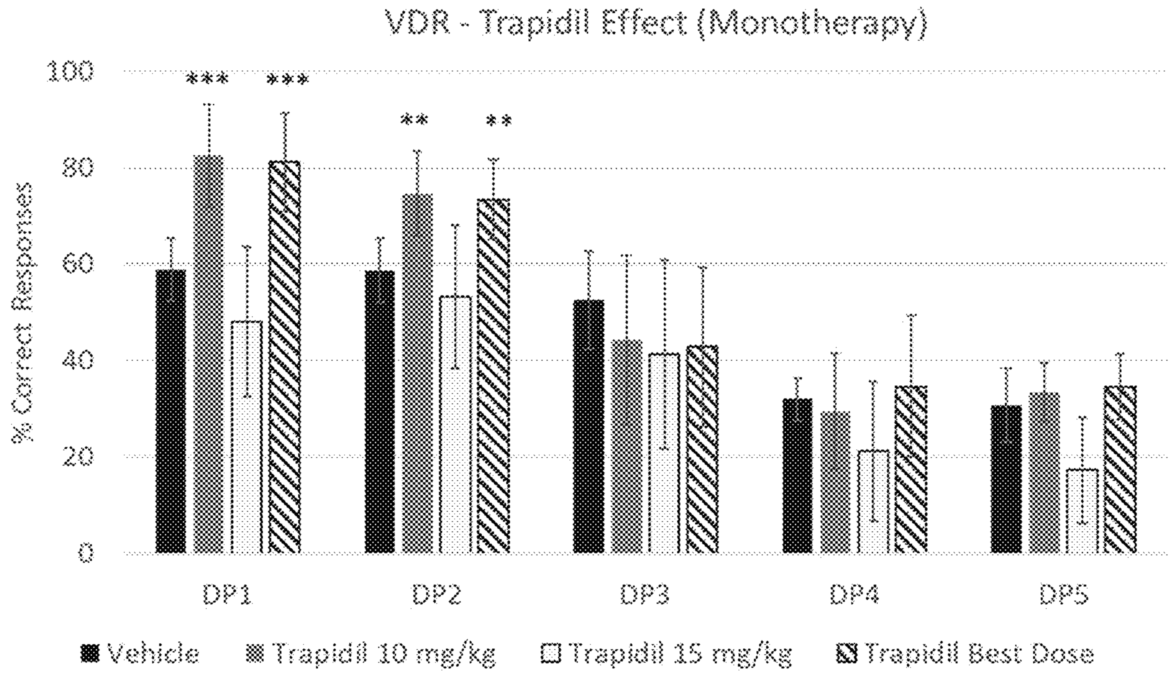
FIG. 5 exemplifies that trapidil as a monotherapy can improve ability of MPTP lesioned primates in the VDR tasks, in particular those at short delay periods (DP1 and DP2). Compared to vehicle: p<0.05, *p<0.01
Figure 6:
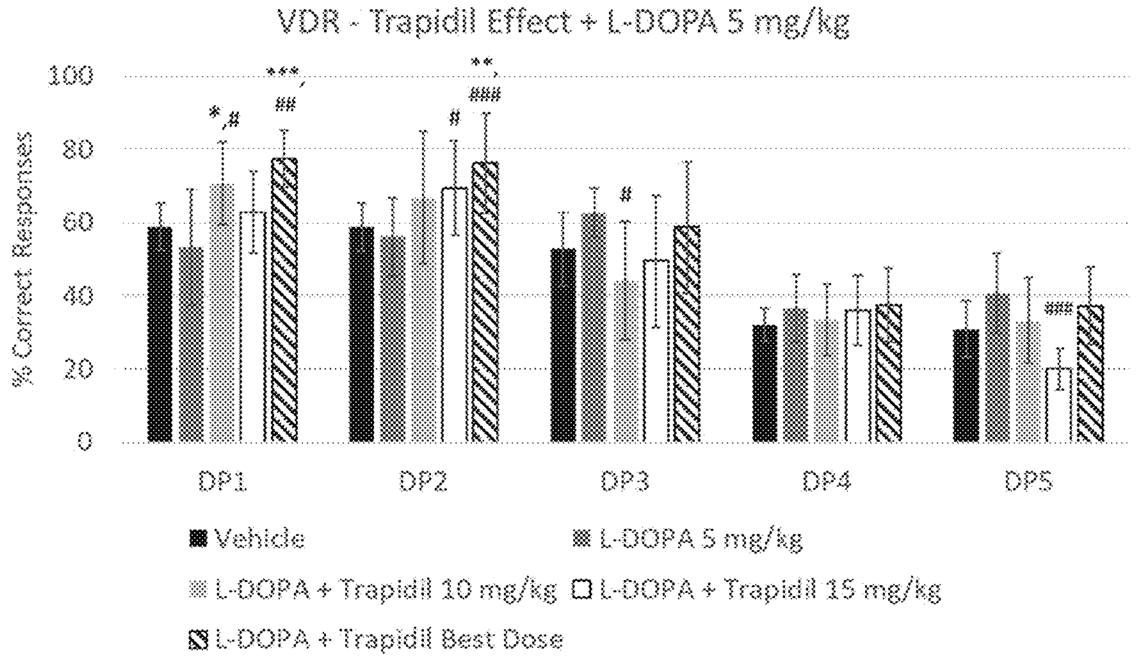
FIG. 6 exemplifies that trapidil in combination with levodopa can also improve ability of MPTP lesioned primates in the VDR tasks, in particular those at short delay periods (DP1 and DP2). Compared to vehicle: *p<0.1, p<0.05, *p<0.01; compared to L-DOPA 5 mg/kg: #p<0.1, ##p<0.05, ###p<0.01
Figure 7:
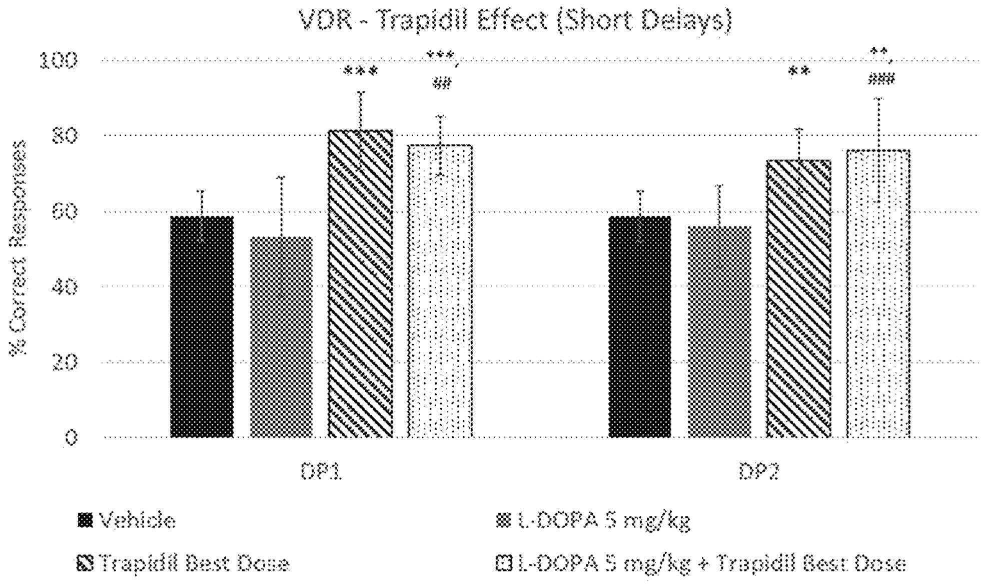
FIG. 7 exemplifies that trapidil at short delay periods improves VDR tasks with or without levodopa. Compared to vehicle: *p<0.1, p<0.05, *p<0.01; compared to L-DOPA 5 mg/kg: #p<0.1, ##p<0.05, ###p<0.01. Note: trapidil monotherapy was not compared to L-DOPA 5 mg/kg FIG. 8 exemplifies that trapidil significantly reduces primate response time on the VDR task. Compared to vehicle: p<0.5, *p<0.01

Trapidil at 10 mg/kg is able to significantly improve accuracy of VDR responses at the two shorter delay periods (FIG. 5). This signifies cognitive improvements in the domains of spatial working memory, executive function, and attention. Further, response accuracy in treatment arms with the combination of low dose levodopa (5 mg/kg) and trapidil further shows that trapidil improves VDR task response at the shorter delay periods (FIG. 6). Ultimately, trapidil shows a great improvement in correct responses for DP1 and DP2, with or without levodopa (FIG. 7). In FIGS. 5-7, "Best dose" designates the best of either 10 or 15 mg/kg for each of the five primates in terms of response to trapidil treatment.

Figure 8:
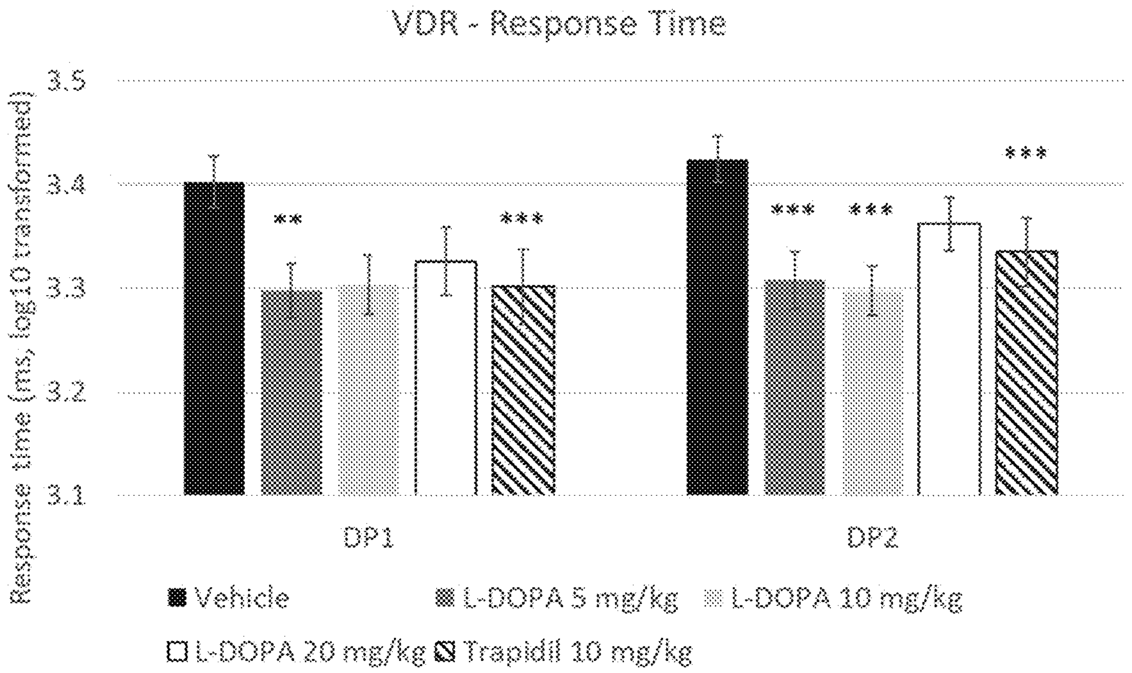

Further, the improvement for the delay periods DP1 and DP2 with trapidil 10 mg/kg monotherapy was investigated in greater detail as that had the strongest effect of any treatment effect. In particular, it was observed that the total response time (from stimulus cue to primate response) of the primates significantly decreased with trapidil (10 mg/kg) (FIG. 8). This decrease suggests an improvement in motivation and enthusiasm, which could potentially correct for the associated psychological condition of apathy in Parkinson's disease. Apathy in Parkinson's disease has been shown to be highly correlated with cognitive impairments in Parkinson's disease and apathy is a predictor of potential cognitive decline. The magnitude of decrease in response time is in line with the maximal decrease in response time by levodopa at any dose, which is a known drug with anti-apathy effects. However, not only were the primates completing the tasks faster on trapidil, but they were also doing so in a more accurate fashion, unlike levodopa (FIG. 7).

Example 5: Efficacy of Trapidil in Treating Cognitive Impairment in the Phencyclidine Induced Murine Model of Schizophrenia Acute administration of phencyclidine (PCP) is an established model for schizophrenia in rodents for assessing various types of deficits, including cognition. It is a common model for assessing potential pharmacological treatments in schizophrenia. Mice and rat exhibit cognitive deficits that can be detected using various behavioral assessments including the Y-maze spontaneous alternation test, which is an assessment of working memory cognitive abilities.

Figure 9A:
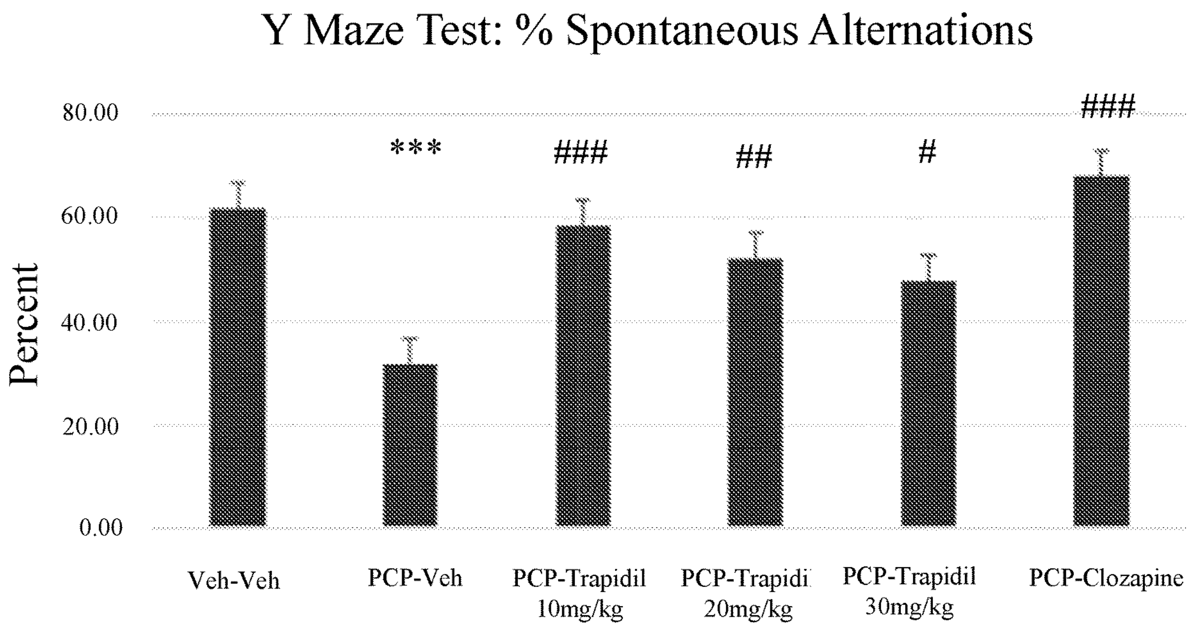
FIG. 9A-9B exemplify that trapidil significantly reduces deficits due to phencyclidine in the murine model of schizophrenia in the Y-maze spontaneous alternations test.
Figure 9B:
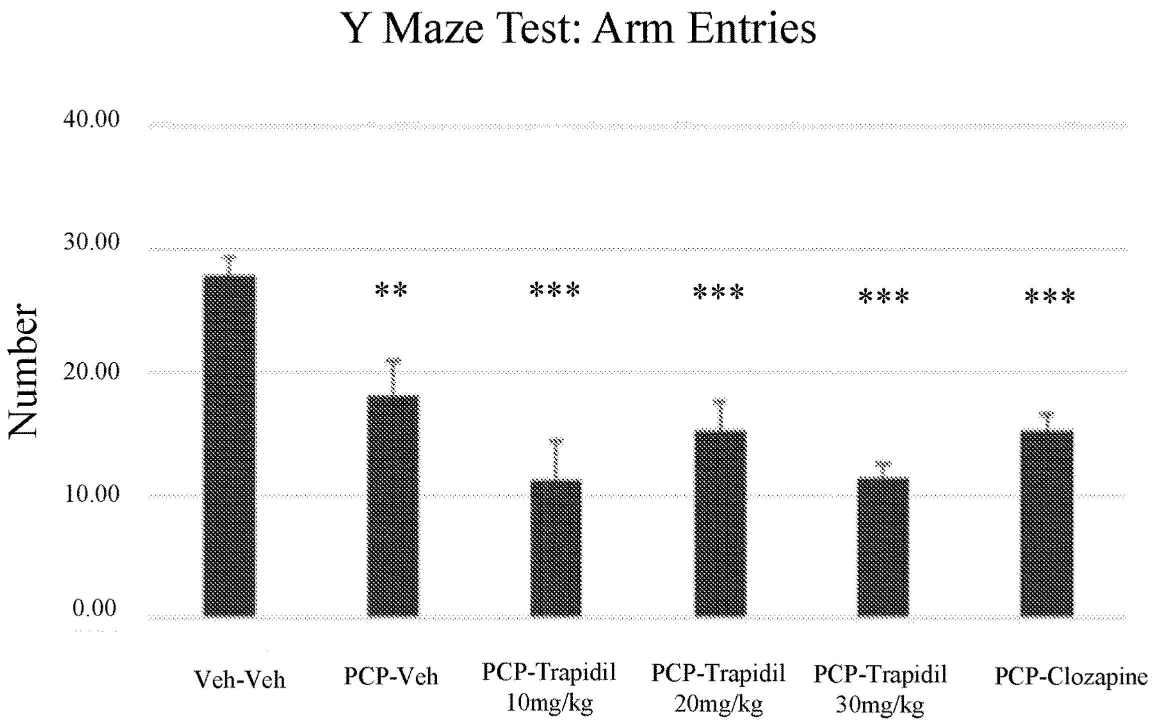

C57BL/6J mice were split into several treatment groups in a dose-ranging study (Table 3). Acute administration of PCP (7.5 mg/kg, IP) induced working memory deficits as detected by decreased percentage of spontaneous alternations (FIG. 9A). Oral administration of trapidil was able to correct the observed deficits in percentage of spontaneous alternations induced by PCP at several different doses. These results are consistent with clozapine (2.5 mg/kg, IP), an atypical antipsychotic, which was used as a positive control. The total number of entries into the Y-maze were also catalogued to assess confounding effects. As there was no significant difference in number of entries versus the PCP group, no such confounding effects were detected (FIG. 9B).

TABLE 3

Treatments for assessing pro-cognitive effects of trapidil in a murine model of schizophrenia.

| Treatment # | Treatment A | Treatment B | # Mice |
|---|---|---|---|
| 1 | Vehicle | Vehicle | 10 |
| 2 | PCP (7.5 mg/kg) | Vehicle | 10 |
| 3 | PCP (7.5 mg/kg) | trapidil (10 mg/kg) | 5 |
| 4 | PCP (7.5 mg/kg) | trapidil (20 mg/kg) | 5 |
| 5 | PCP (7.5 mg/kg) | trapidil (30 mg/kg) | 5 |
| 6 | PCP (7.5 mg/kg) | Clozapine (2.5 mg/kg) | 10 |

Example 6. Treating Dementia with Trapidil

A patient diagnosed with dementia is administered a therapeutically effective dose of trapidil, a derivative of trapidil, a metabolite of trapidil, a prodrug of trapidil, an analog of trapidil, or a pharmaceutically acceptable salt of trapidil. In some embodiments, the therapeutically effective dose of trapidil, the metabolite of trapidil, the prodrug of trapidil, the analog of trapidil, or the pharmaceutically acceptable salt of trapidil, is no more than 200 milligrams administered three times a day.

In some embodiments, the patient has also been diagnosed with Parkinson's disease. In this example, the dementia is not caused by the Parkinson's disease. In some embodiments, the patient is also administered a therapeutically effective dose of a dopamine precursor (e.g., levodopa) or dopamine agonist, with or without an adjunctive therapy (e.g., carbidopa), to treat the Parkinson's disease. In some embodiments, the dose of levodopa is a subclinical dose when administered in combination with the dose of the trapidil, the derivative of trapidil, the metabolite of trapidil, the prodrug of trapidil, the analog of trapidil, or the pharmaceutically acceptable salt of trapidil.

In some embodiments, the patient has also been diagnosed with schizophrenia. In some embodiments, the patient is also administered a therapeutically effective dose of an antipsychotic (e.g., aripiprazole) to treat the schizophrenia. In some embodiments, the dose of aripiprazole is a subclinical dose when administered in combination with the dose of the trapidil, the derivative of trapidil, the metabolite of trapidil, the prodrug of trapidil, the analog of trapidil, or the pharmaceutically acceptable salt of trapidil.

Example 7. Treating Apathy with Trapidil

A patient diagnosed with apathy is administered a therapeutically effective dose of trapidil, a derivative of trapidil, a metabolite of trapidil, a prodrug of trapidil, an analog of trapidil, or a pharmaceutically acceptable salt of trapidil. In some embodiments, the therapeutically effective dose of trapidil, the metabolite of trapidil, the prodrug of trapidil, the analog of trapidil, or the pharmaceutically acceptable salt of trapidil, is no more than 200 milligrams administered three times a day.

In some embodiments, the patient has also been diagnosed with Parkinson's disease. In this example, the apathy is not caused by the Parkinson's disease. In some embodiments, the patient is also administered a therapeutically effective dose of a dopamine precursor (e.g., levodopa) or dopamine agonist, with or without an adjunctive therapy (e.g., carbidopa), to treat the Parkinson's disease. In some embodiments, the dose of levodopa is a subclinical dose when administered in combination with the dose of the trapidil, the derivative of trapidil, the metabolite of trapidil, the prodrug of trapidil, the analog of trapidil, or the pharmaceutically acceptable salt of trapidil.

In some embodiments, the patient has also been diagnosed with schizophrenia. In some embodiments, the patient is also administered a therapeutically effective dose of an antipsychotic (e.g., aripiprazole) to treat the schizophrenia. In some embodiments, the dose of aripiprazole is a subclinical dose when administered in combination with of the trapidil, the derivative of trapidil, the metabolite of trapidil, the prodrug of trapidil, the analog of trapidil, or the pharmaceutically acceptable salt of trapidil.

Example 8. Treating or Preventing Drug-Induced Cognitive Deficits in a Parkinson's Disease Patient In a Parkinson's disease patient, cognitive deficits have been caused or worsened by administration of clinical dosage amounts of levodopa and/or carbidopa for the treatment of the Parkinson's disease. To treat the cognitive deficits, a therapeutically effective amount of trapidil, a derivative of trapidil, a metabolite of trapidil, a prodrug of trapidil, an analog of trapidil, or a pharmaceutically acceptable salt of trapidil is administered to the patient. Cognitive performance in the patient improves following the administration of the therapeutically effective amount of the derivative of trapidil, the metabolite of trapidil, the prodrug of trapidil, the analog of trapidil, or the pharmaceutically acceptable salt of trapidil.

In some embodiments, the trapidil, the prodrug of trapidil, the analog of trapidil, or the pharmaceutically acceptable salt of trapidil potentiates the therapeutic effects of the levodopa and/or carbidopa in the patient for the treatment of the Parkinson's disease, such that lower (subclinical) dosage amounts of the levodopa and/or carbidopa are needed over time to treat the Parkinson's disease. Thus, the administration of the trapidil, the prodrug of trapidil, the analog of trapidil, or the pharmaceutically acceptable salt of trapidil is effective to prevent the cognitive deficits in the patient that are caused or worsened by the administration the clinical dosage amounts of levodopa and/or carbidopa.

What is claimed:

1. A method of treating a cognitive impairment in a subject that has Parkinson's disease, schizophrenia, or Attention-Deficit/Hyperactivity Disorder, comprising administering to the subject a therapeutically effective dose of trapidil, deuterated trapidil, or a pharmaceutically acceptable salt thereof.

2. The method of claim 1, further comprising administering to the subject an additional therapeutic agent that is: a dopamine precursor; a dopamine agonist; or a combination thereof.

3. The method of claim 2, wherein the dopamine precursor is levodopa.

4. The method of claim 1, wherein the cognitive impairment is a deficit in: attention, working memory, executive function, visuospatial function, or memory, or any combination thereof.

5. The method of claim 1, wherein the cognitive impairment is slowed thinking, slowed speech, difficulties in word-finding, or any combination thereof.

6. The method of claim 1, wherein the pharmaceutically acceptable salt is a salt with hydrochloric acid, hydrobromic acid, hydroiodic acid, sulfuric acid, nitric acid, oxalic acid, malonic acid, or tartaric acid.

7. The method of claim 1, wherein the trapidil, the deuterated trapidil, or the pharmaceutically acceptable salt thereof is administered orally, intravenously, or subcutaneously.

8. The method of claim 2, wherein the trapidil, the deuterated trapidil, or the pharmaceutically acceptable salt thereof, and the additional therapeutic agent are administered simultaneously.

9. The method of claim 2, wherein the trapidil, the deuterated trapidil, or the pharmaceutically acceptable salt thereof, and the additional therapeutic agent are administered sequentially.

10. The method of claim 1, wherein the therapeutically effective dose comprises less than or equal to about 200 milligrams.

11. The method of claim 1, wherein the cognitive impairment is not caused by administration of levodopa.

12. The method of claim 1, wherein the subject has the Parkinson's disease.

13. The method of claim 1, wherein the subject has the schizophrenia.

14. The method of claim 1, wherein the subject has the Attention-Deficit/Hyperactivity Disorder.

15. The method of claim 1, further comprising administering to the subject an antidepressant agent.

16. The method of claim 15, wherein the trapidil, the deuterated trapidil, or the pharmaceutically acceptable salt thereof, and the antidepressant agent are administered sequentially.

17. The method of claim 1, further comprising administering to the subject an antipsychotic agent.

18. The method of claim 17, wherein the trapidil, the deuterated trapidil, or the pharmaceutically acceptable salt thereof, and the antipsychotic agent are administered sequentially.

19. The method of claim 1, further comprising administering to the subject an anxiolytic agent.

20. The method of claim 19, wherein the trapidil, the deuterated trapidil, or the pharmaceutically acceptable salt thereof, and the anxiolytic agent are administered sequentially.

* * * * *